United States Patent [19]
Holcomb

[11] Patent Number: 5,312,321
[45] Date of Patent: May 17, 1994

[54] METHOD AND APPARATUS FOR SUPPRESSING NEURON ACTION POTENTIAL FIRINGS

[75] Inventor: Robert R. Holcomb, Hackleburg, Ala.

[73] Assignee: Holcomb Technology, Inc., Nashville, Tenn.

[21] Appl. No.: 880,872

[22] Filed: May 11, 1992

Related U.S. Application Data

[63] Continuation-in-part of Ser. No. 503,318, Apr. 2, 1990, abandoned, which is a continuation-in-part of Ser. No. 171,837, Mar. 22, 1988, abandoned, which is a continuation-in-part of Ser. No. 939,950, Dec. 9, 1986, abandoned, which is a continuation-in-part of Ser. No. 934,568, Nov. 21, 1986, abandoned.

[51] Int. Cl.$^5$ ............................................. A61B 17/52
[52] U.S. Cl. ........................................................ 600/9
[58] Field of Search .................................... 600/9–15

[56] References Cited

U.S. PATENT DOCUMENTS

| | | |
|---|---|---|
| 272,904 | 2/1883 | Russell . |
| 3,921,620 | 11/1975 | Nakayama . |
| 3,943,912 | 3/1976 | Nakayama . |
| 4,162,672 | 7/1979 | Yazaki . |
| 4,330,892 | 5/1982 | Fukushima . |
| 4,480,596 | 11/1984 | Shumiyashu . |
| 4,489,711 | 12/1984 | Latzke . |
| 4,509,219 | 4/1985 | Yagi . |
| 4,549,532 | 10/1985 | Baerman . |
| 4,587,956 | 5/1986 | Griffin et al. . |

FOREIGN PATENT DOCUMENTS

| | | |
|---|---|---|
| 0081109 | 6/1983 | European Pat. Off. ............... 600/15 |
| 100050 | 8/1984 | European Pat. Off. . |
| 0244784 | 11/1987 | European Pat. Off. . |
| 334141 | 9/1989 | European Pat. Off. . |
| 428474 | 5/1991 | European Pat. Off. . |
| 3402838A | 4/1985 | Fed. Rep. of Germany . |
| 3828043 | 5/1989 | Fed. Rep. of Germany . |
| 2308384 | 11/1976 | France . |
| 2370483 | 6/1978 | France . |
| 2595942 | 9/1987 | France . |
| WO91/15263 | 10/1991 | PCT Int'l Appl. . |
| 676288 | 7/1979 | U.S.S.R. . |
| 787042 | 12/1980 | U.S.S.R. . |
| 429944 | 1/1935 | United Kingdom . |
| 2196855 | 5/1988 | United Kingdom . |

*Primary Examiner*—Lee S. Cohen
*Assistant Examiner*—J. P. Lacyk
*Attorney, Agent, or Firm*—Howrey & Simon

[57] ABSTRACT

A device and a method for suppressing nerve cell action potentials is provided. An octapolar magnetic device is disposed near a mammalian sensory neuron so that the magnetic field generated by one quadrapolar face of the device is symmetrically disposed about the neuron. The magnetic device is comprised of four magnetic bodies, each having two opposite magnetic poles. Two positive and two negative magnetic poles are disposed substantially in a single plane and to define the four vertices of a quadrilateral shape, the two positive poles defining two diagonal vertices, and the two negative poles defining the opposite two diagonal vertices of the quadrilateral shape. A housing is provided to hold the magnetic bodies in a fixed relative position and thus maintain the quadrilateral orientation of the poles.

14 Claims, 30 Drawing Sheets

FIG. 10
(SURFACE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | .0 | 0 | 0 | 0 | 0 | 0 | 0 | 0 | 0 | 0 | 0 |
| 0 | 0 | 0 | -1 | -4 | -2 | +10 | +20 | +10 | +10 | 0 | 0 |
| 0 | 0 | -1 | -4 | -10 | +18 | -19 | +23 | +10 | +3 | +2 | 0 |
| 0 | 0 | -1 | -5 | +39 | N +1928 | S -1800 | -36 | +8 | +1 | 0 | 0 |
| 0 | 0 | +1 | +3 | -9 | -1988 S | +1900 N | +61 | -5 | -1 | 0 | 0 |
| 0 | +1 | +2 | +6 | +16 | -20 | -6 | -26 | -8 | -1 | 0 | 0 |
| 0 | +1 | +1 | +3 | +6 | +5 | -4 | -6 | -3 | 0 | 0 | 0 |
| 0 | 0 | 0 | +1 | +1 | 0 | -1 | -2 | -2 | -1 | 0 | 0 |
| 0 | 0 | 0 | 0 | +1 | +1 | -1 | -2 | -1 | -1 | 0 | 0 |
| 0 | 0 | 0 | 0 | 0 | 0 | 0 | 0 | 0 | 0 | 0 | 0 |

FIG. 11
(0.4" ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | +1 | 0 |
| 0 | 0 | 0 | 0 | 0 | 0 | 0 | +1 | +2 | +1 | +1 | 0 |
| 0 | 0 | 0 | 0 | +2 | +3 | -1 | -1 | +1 | +1 | +1 | 0 |
| 0 | 0 | +1 | +2 | +12 | +33 | -33 | -18 | -1 | +1 | +1 | 0 |
| 0 | 0 | +1 | +2 | +43 | N +149 | S -118 | -82 | -2 | +1 | +1 | 0 |
| 0 | 0 | -1 | -3 | -19 | -133 S | +118 N | +98 | +4 | +1 | 0 | 0 |
| 0 | 0 | 0 | -1 | -22 | -196 | +28 | +33 | +2 | 0 | 0 | 0 |
| 0 | 0 | 0 | 0 | -2 | -8 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |

FIG. 12
(0.8" ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | +1 | +3 | +2 | -2 | -4 | -2 | 0 | 0 | 0 |
| 0 | 0 | 0 | +2 | +10 | +17 | -11 | -19 | -4 | -1 | 0 | 0 |
| 0 | 0 | 0 | +3 | +16 | N +27 | S -18 | -17 | -3 | 0 | 0 | 0 |
| 0 | 0 | 0 | -2 | -6 | S -21 | +11 N | +14 | +3 | 0 | 0 | 0 |
| 0 | 0 | -1 | -3 | -14 | -23 | +6 | +13 | +3 | 0 | 0 | 0 |
| 0 | 0 | -1 | -2 | -5 | -6 | -1 | +2 | +1 | 0 | 0 | 0 |
| 0 | 0 | 0 | 0 | -1 | -2 | 0 | 0 | 0 | -1 | 0 | -1 |
| 0 | 0 | 0 | 0 | 0 | -1 | 0 | 0 | 0 | 0 | 0 | 0 |
| 0 | 0 | 0 | 0 | 0 | 0 | 0 | 0 | 0 | 0 | 0 | 0 |

FIG. 13
(1.2" ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | -1 | 0 | 0 | 0 |
| 0 | 0 | 0 | +1 | +2 | +1 | -2 | -2 | -2 | 0 | 0 | 0 |
| 0 | 0 | 0 | +2 | +5 | +3 | -9 | -5 | -2 | -1 | 0 | 0 |
| 0 | 0 | 0 | +2 | +5 | N +4 | S -4 | -4 | -2 | 0 | 0 | 0 |
| 0 | 0 | 0 | -1 | -3 | S -2 | +1 N | +2 | 0 | 0 | 0 | 0 |
| 0 | 0 | -1 | -3 | -6 | -6 | +2 | +4 | +1 | 0 | 0 | 0 |
| 0 | 0 | -1 | -3 | -4 | -3 | 0 | +2 | +1 | 0 | 0 | 0 |
| 0 | 0 | 0 | -1 | -2 | -2 | 0 | 0 | 0 | 0 | 0 | 0 |
| 0 | 0 | 0 | 0 | 0 | -1 | 0 | 0 | 0 | 0 | 0 | 0 |
| 0 | 0 | 0 | 0 | 0 | 0 | 0 | 0 | 0 | 0 | 0 | 0 |

FIG. 14
(1.6" ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | 0 | +1 | +1 | 0 | -1 | -1 | 0 | 0 | 0 |
| 0 | 0 | 0 | +1 | +2 | +1 | -1 | -2 | -1 | -1 | 0 | 0 |
| 0 | 0 | 0 | 0 | +1 | N +1 | S -1 | -1 | -1 | 0 | 0 | 0 |
| 0 | 0 | 0 | 0 | -1 | S 0 | 0 N | 0 | 0 | 0 | 0 | 0 |
| 0 | 0 | -1 | -1 | -2 | -2 | 0 | +1 | 0 | 0 | 0 | 0 |
| 0 | 0 | 0 | -1 | -2 | -2 | 0 | 0 | 0 | 0 | 0 | 0 |
| 0 | 0 | 0 | 0 | -1 | -1 | 0 | 0 | 0 | 0 | 0 | 0 |
| 0 | 0 | 0 | 0 | -1 | 0 | 0 | 0 | 0 | 0 | 0 | 0 |
| 0 | 0 | 0 | 0 | 0 | 0 | 0 | 0 | 0 | 0 | 0 | 0 |

FIG. 15
(2" ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | +1 | 0 | 0 | 0 | -1 | -1 | 0 | 0 | 0 |
| 0 | 0 | 0 | 0 | 0 | N 0 | S 0 | 0 | 0 | 0 | 0 | 0 |
| 0 | 0 | 0 | 0 | 0 | S -1 | 0 N | 0 | 0 | 0 | 0 | 0 |
| 0 | 0 | 0 | 0 | -1 | 0 | 0 | 0 | 0 | 0 | 0 | 0 |
| 0 | 0 | 0 | 0 | -1 | 0 | 0 | 0 | 0 | 0 | 0 | 0 |
| 0 | 0 | 0 | 0 | 0 | 0 | +1 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |

FIG. 16
(2.75" ABOVE)

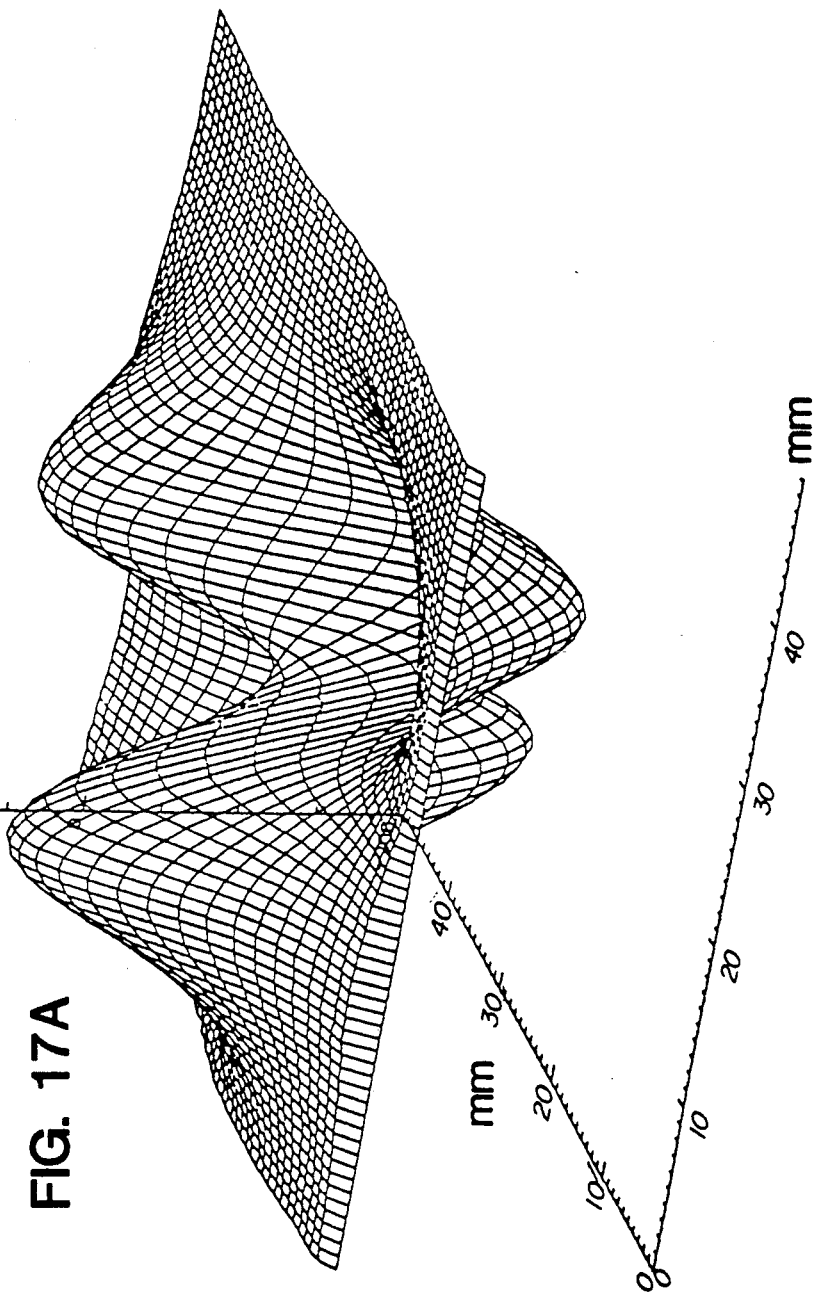
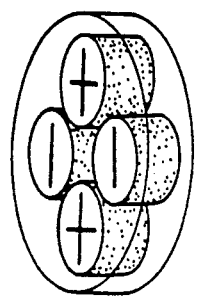
FIG. 17B
FIG. 17A

FIG. 19A PRE

POST

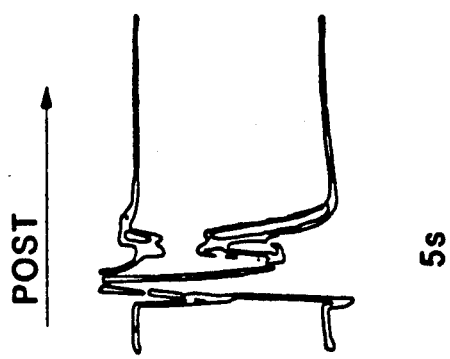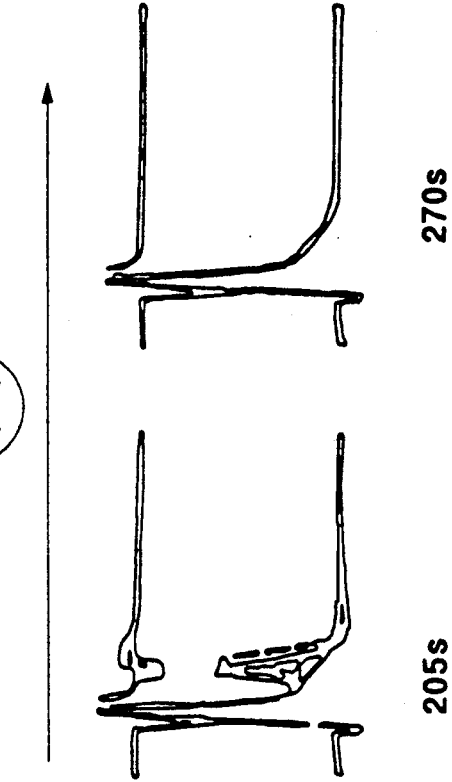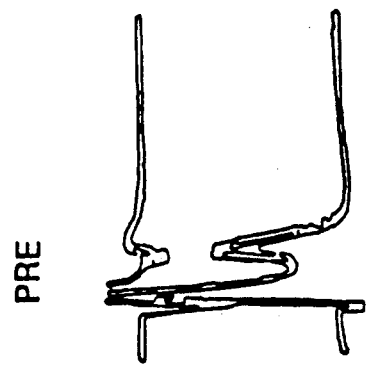
FIG. 23A  FIG. 23B  FIG. 23C  FIG. 23D

DOTS = CHARGE CENTERS

MAGNABLOC　　　　　WAFFLE (50 stimuli at 1 Hz, or 50 sec, per period)

METHOD AND APPARATUS FOR SUPPRESSING NEURON ACTION POTENTIAL FIRINGS

This application is a continuation-in-part of U.S. Pat. application Ser. No. 07/503,318, filed Apr. 2, 1990, now abandoned, which is a continuation-in-part of U.S. patent application Ser. No. 171,837, filed Mar. 22, 1988, now abandoned, which is a continuation-in-part of U.S. patent application Ser. No. 939,950, filed Dec. 9, 1986, now abandoned which is a continuation-in-part of U.S. patent application Ser. No. 934,568, filed Nov. 21, 1986 now abandoned.

BACKGROUND OF THE INVENTION

The present invention relates to a magnetic device having four cylindrical, center face charged, magnetic bodies disposed in an array of alternating polarity and contained in a holder. The invention also relates to a method for using the magnetic device to suppress the firing of action potentials of mammalian sensory neurons.

There is a difference in electrical potential across the cell membrane of a sensory neuron, or nerve cell. When a neuron receives an impulse transmitted from another neuron, the electric potential difference across the cell membrane is dramatically reduced and generally reverses. This reduction and reversal of potential is referred to as the firing of the neuron's action potential. If such action potential firings are suppressed, the transmission of nerve impulses are also suppressed.

Magnetic stimulation of nerve cells has been accomplished with devices such as the Cadwell Magneto-Electric Stimulator (MES-10) manufactured by Cadwell Laboratories, Inc. of Kennewick, Wash. Recent studies indicate that static magnetic fields can alter the behavior of nerve tissues. In a study described in Hong, Harmon & Yu: *Static Magnetic Field Influence on Rat Tail Nerve Function*, 67 Arch. Phys. Med. Rehabil. 746–49 (1986), a homogenous static magnetic field with a magnitude of greater than 0.5 Tesla (T) was found to alter nerve function when applied for a duration of at least 30 s. The Hong study postulates that an electromagnetic field may relieve pain by selectively increasing the excitability of large nerve fibers, which (according to the gate control theory) may block the gate for pain. This study also suggests that static magnetic fields alter nerve function by stabilizing nerve cell membranes and the permeability of the membranes to certain ions whose transmission through the cell membrane results in the firing of action potentials.

Pain sensations can be a result of improper nerve function, as when such pain is caused by inordinately excitable nerve cells or by nerve cells having cell wall membranes that leak ions. Pain sensations may also be caused by damaged nerve cells. For example, nerve cells can be damaged by post-operative scarring or by physical impingement, commonly associated with degenerative disc disease. Even when nerves function properly, chronic pain sensations are initiated through nerve cells. Thus, new ways of altering nerve cell function, as for example by stabilizing nerve cell wall membranes, may facilitate treatment of pain.

SUMMARY OF THE INVENTION

In accordance with the principles of the present invention, as embodied and as broadly described herein, a device and a method for suppressing nerve cell action potentials is provided. According to the invention, a magnetic device is disposed near a mammalian sensory neuron so that the magnetic field generated by one quadrapolar face of the device is symetrically disposed about the neuron. During such placement and for a period thereafter, the neuron action potentials are suppressed. The magnetic device is comprised of four magnetic bodies, each having two opposite magnetic poles. Two positive and two negative magnetic poles are disposed substantially in a single plane and to define the four vertices of a quadrilateral shape, the two positive poles defining two diagonal vertices, and the two negative poles defining the opposite two diagonal vertices of the quadrilateral shape. A housing is provided to hold the magnetic bodies in a fixed relative position and thus maintain the quadrilateral orientation of the poles.

Each of the four magnetic bodies is cylindrical and has opposing center-charged faces. The proximity of the individual magnets within the device must be maintained. If the individual magnets are separated or the device is brought into close proximity with other magnets, the magnetic field and its gradient will be changed so that the device will not perform properly.

BRIEF DESCRIPTION OF THE DRAWINGS

Figure 16:
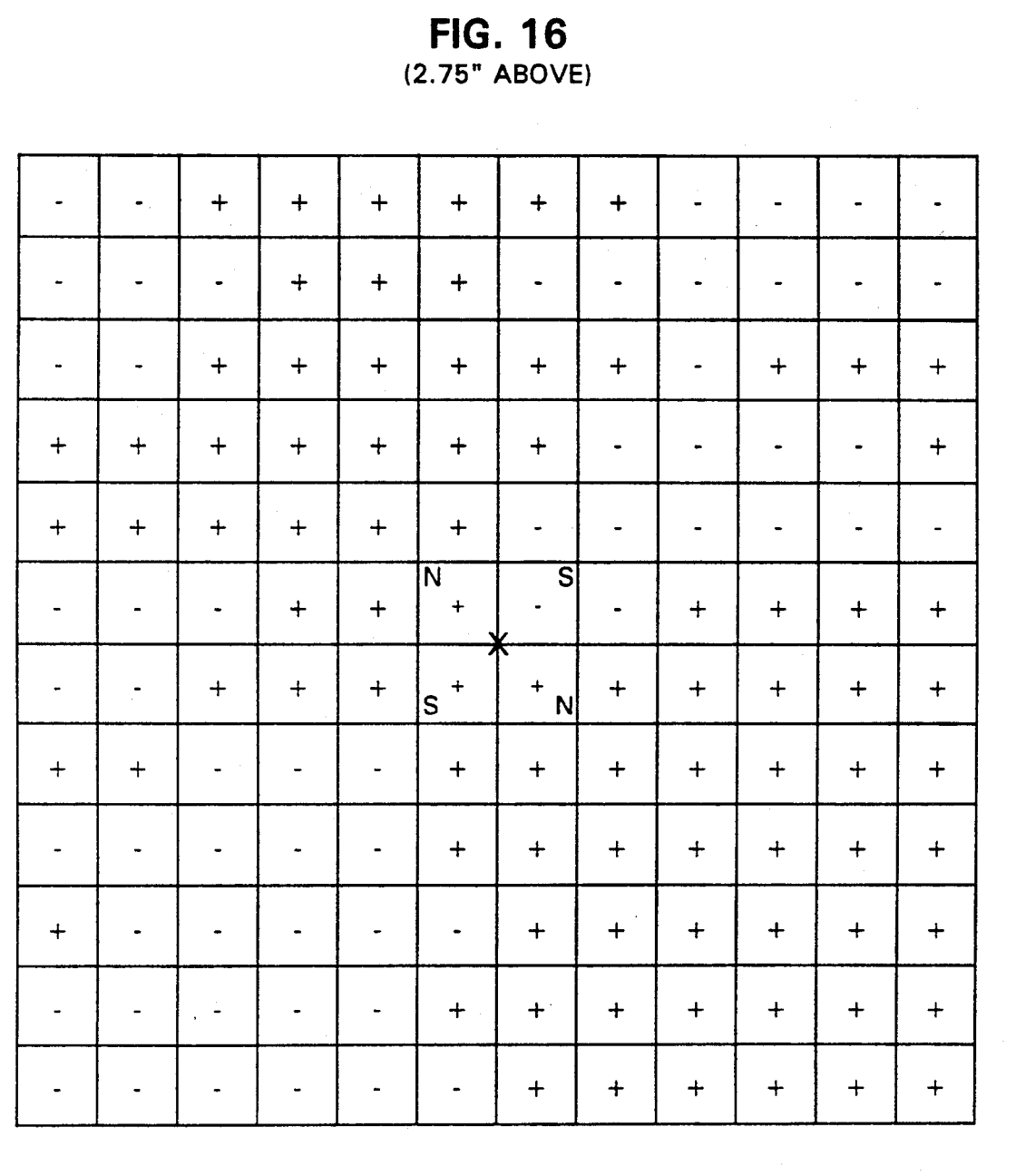

FIGS. 10-16 are grids of magnetic field measurements taken at various distances from the surface of the magnetic device of FIG. 2.

FIGS. 17A-B are an illustration of the magnetic field of magnetic device of FIG. 2, and another illustration of the device of FIG. 2, respectively.

FIGS. 19A-G show oscilloscope traces from tests on mammalian nerve cells conducted using the magnetic device of FIG. 2.

FIGS. 20A to 23D show oscilloscope traces from tests on mammalian neurons conducted using magnetic devices different from that shown in FIG. 2.

DETAILED DESCRIPTION

Figure 1:
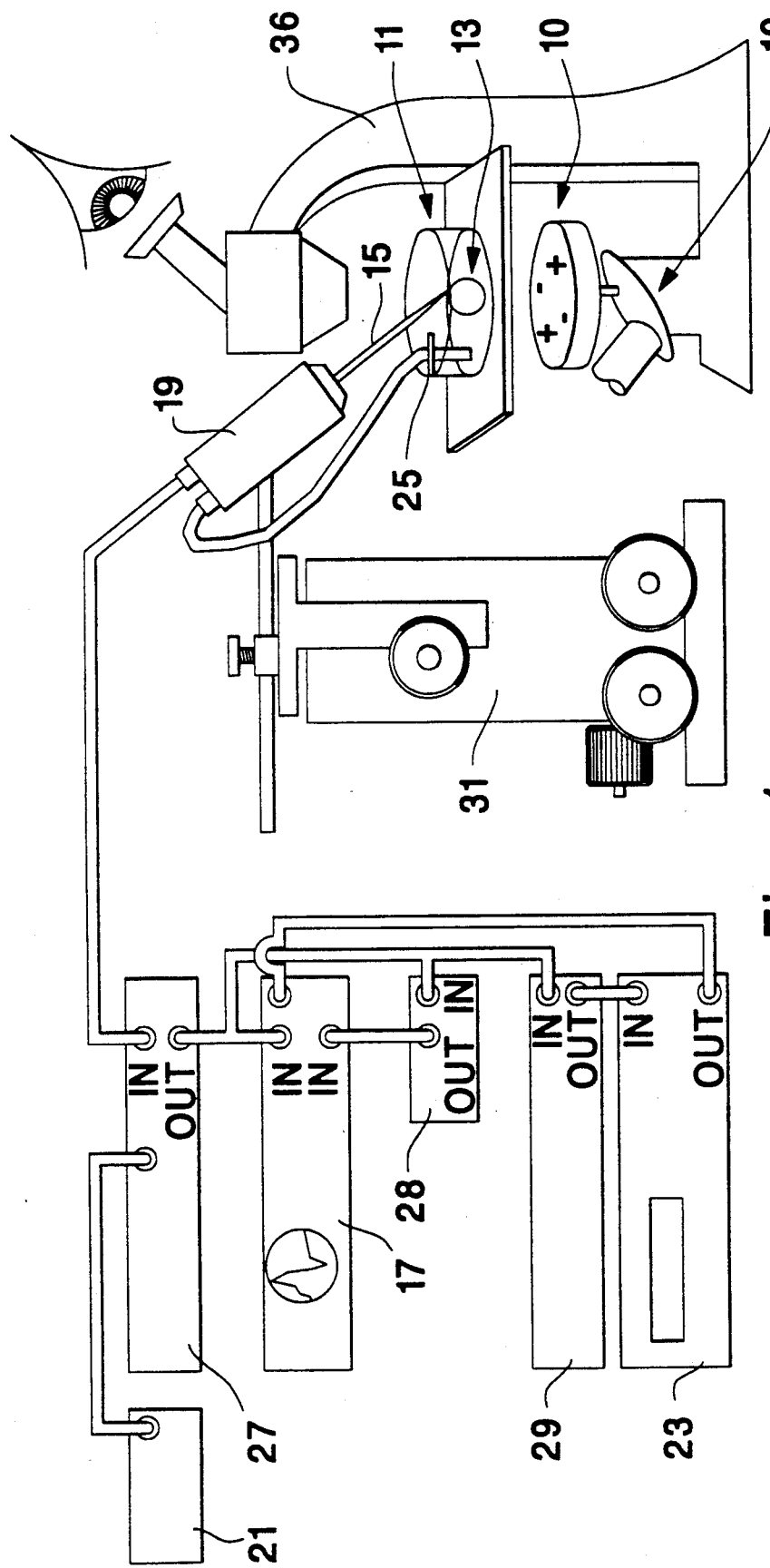
FIG. 1 is a schematic illustration of an experimental design used to monitor the suppression of nerve cell action potentials with the method of the present invention.

Reference will now be made in detail to the presently preferred embodiments of the invention, examples of which are illustrated in the accompanying drawings. Throughout the drawings, like reference characters are used to designate like elements.

DESCRIPTION AND CHARACTERIZATION OF THE MAGNETIC DEVICE

A first embodiment of the permanent magnetic device of the invention is illustrated in FIGS. 2–5. In this embodiment, the magnetic device 10 comprises four magnetic bodies 12, 14, 16, and 18 that are oriented and held in a housing 20 that can be easily handled without altering the arrangement of the magnetic bodies. Each of the magnetic bodies is a cylindrical, center-charged permanent magnet and the magnets are of equal size and strength. The magnetic poles are disposed substantially in two parallel planes, with each plane containing opposing positive and negative magnetic poles. Collectively, the four magnetic bodies form a magnetic octapole.

Figure 2:
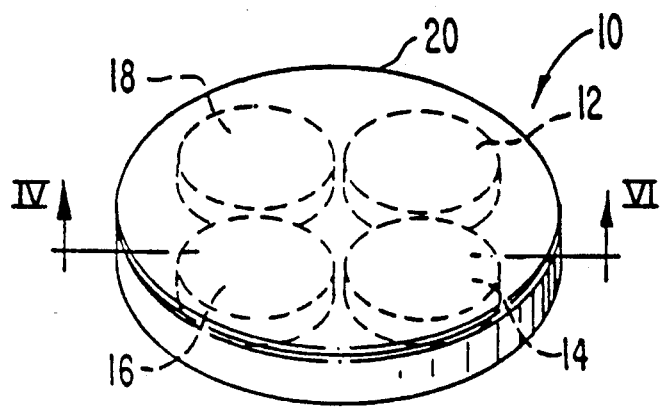
FIG. 2 is a perspective view of a first embodiment of a magnetic device in accordance with the principles of the invention.
Figure 3:
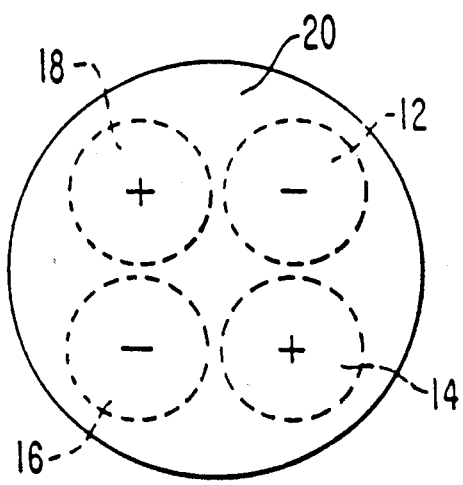
FIG. 3 is a plan view of the magnetic device of FIG. 2.
Figure 5:
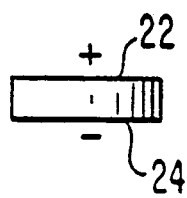
FIG. 5 is a side elevation of one of the magnetic bodies of the magnetic device of FIG. 2.

As shown in FIG. 5, one face 22 of each magnetic body is positively center charged, and the opposite face 24 is negatively center charged. Thus, a positive magnetic pole is centered on face 22, while a negative magnetic pole is centered on face 24. The four magnetic bodies are oriented to define four vertices of a quadrilateral shape. As shown in FIGS. 2 and 3, the four magnetic poles in each of the two parallel planes comprise two positive and two negative poles, the two positive poles defining two diagonal vertices and the two negative poles defining the diagonal vertices of the quadrilateral shape. The distance between the poles in each plane is such that the magnetic field generated by each pole has a significant magnitude at each of the other poles.

Figure 4:
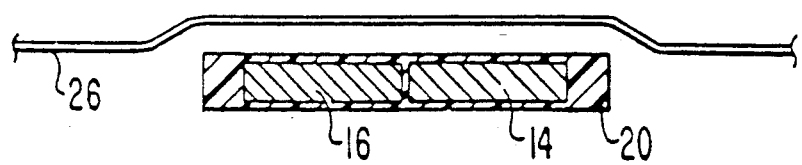
FIG. 4 is a cross-sectional view taken along the line III—III of FIG. 2.

As shown in FIG. 4, the positively charged faces of magnetic bodies 14 and 18 and the negatively charged faces of magnetic bodies 12 and 16 are in a single plane. The two positive poles on faces 14 and 18 define opposite diagonal vertices of the quadrilateral shape, while the two negative poles on the faces of magnetic bodies 12 and 16 define opposite diagonal vertices. Each of the four magnetic poles is magnetically attracted by the two oppositely charged poles and is magnetically repelled by the like charged pole.

Preferably, the magnetic bodies are of equal diameter, which may be within the range of 0.25" (0.63 cm) to 0.50" (1.27 cm). However, much smaller magnetic bodies can be effective. It is further preferred that the magnetic bodies are of equal thickness. The magnetic bodies may be relatively thin with respect to their diameter, to provide a relatively flat magnetic device. The ratio of thickness to diameter may be 0.5:1, although higher and lower ratios are also effective. When cylindrical magnetic bodies with opposite poles on opposite faces are utilized in the invention, both sides of magnetic device 10 will exhibit the same magnetic field. Thus, each face of the octapolar device can be considered to have a quadrapolar configuration.

As the artisan will recognize, permanent magnets are typically formed of ferromagnetic materials. The strength of the magnetic field generated at a given distance from a permanent magnet depends on the properties of the magnet's materials and on the geometry of the magnet. The properties of a ferromagnetic material are customarily represented by the material's demagnetization curve, which is the portion of the hysteresis curve (magnetic induction (B) vs. magnetic field strength (H)) in the second quadrant, as the magnetization is reduced from saturation. A schematic demagnetization curve for neodymium-iron-boron (referred to herein simply as neodymium) is compared in FIG. 33 to curves for samarium-cobalt, Alnico, and ferrite.

The demagnetization curve illustrates three related properties of each material. The first is the material's remanent magnetization, which is the point at which the curve intersects the vertical axis. A common remanent magnetization value for neodymium is 13 kG. The second is the material's coercivity, which is the point at which the curve intersects the horizontal axis. A typical value for neodymium is 14 kOe. The third property is the material's energy product, which is the maximum value of the product BH. The energy product represents the magnetic energy stored in a permanent magnet material. As is apparent from FIG. 33, neodymium has the highest energy product of the materials shown, with samarium-cobalt somewhat lower, and Alnico and ferrite much lower. Typical energy products are 25–40 MG-Oe for neodymium and 20 MG-Oe for samarium-cobalt.

Figure 33:
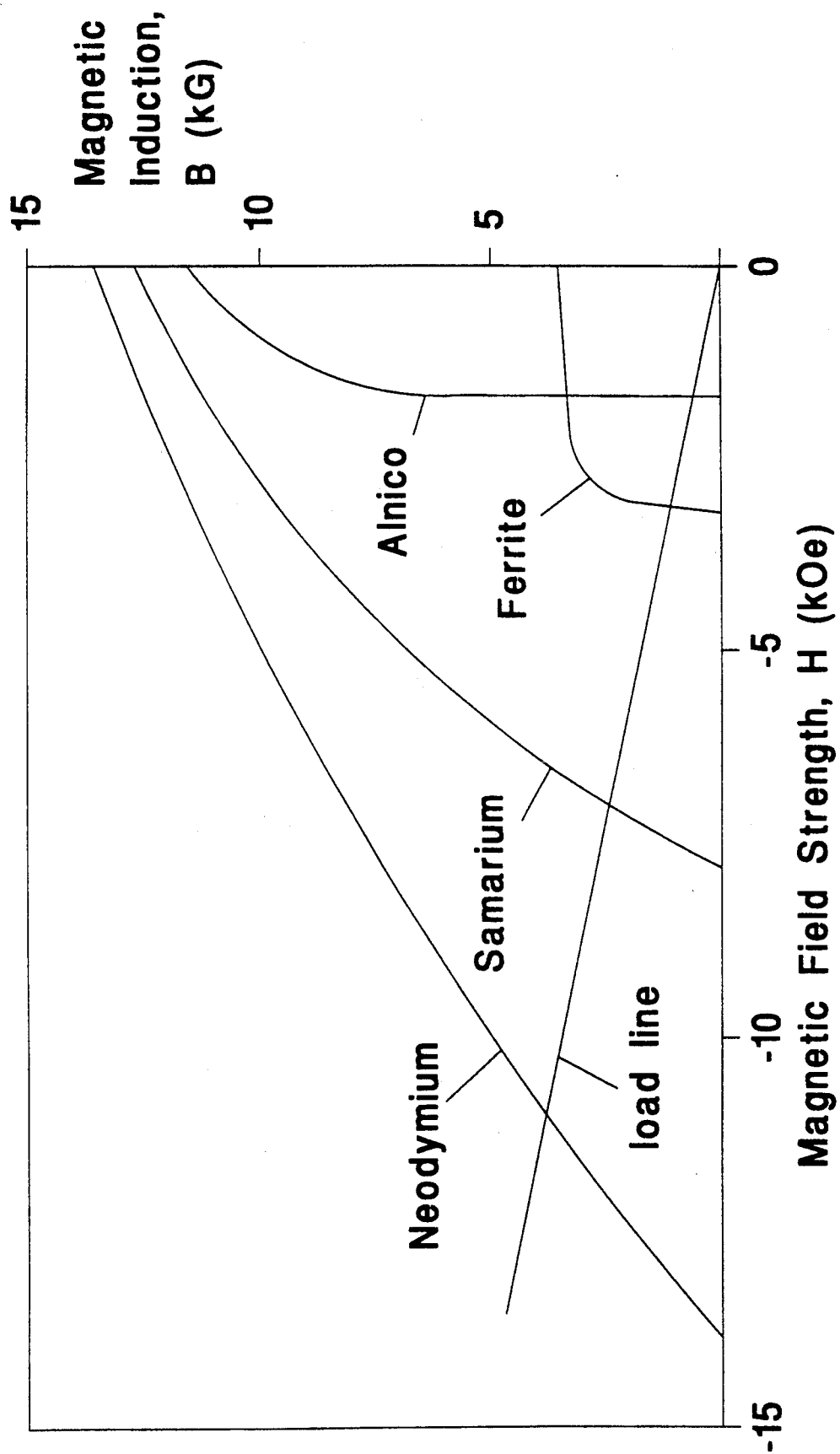
FIG. 33 illustrates a schematic demagnetization curve for various ferromagnetic materials.

As is well known in the art, the strength of the demagnetizing field of a permanent magnet is an open-circuit configuration depends on the shape of the permanent magnet. The geometry of the magnet determines the demagnetizing factor $N_d$, which in turn dictates the load line of the magnet, which is the locus of possible operating points of the magnet. As shown in FIG. 33, the load line passes through the origin on the B, H plane and has a slope that is inversely related to the demagnetizing factor, $N_d$. For a magnet having a geometry such as those shown in FIG. 2, i.e., having a small length-to-diameter ratio, $N_d$ is relatively large, such as 0.5. The slope of the load line is thus relatively shallow. The intersection of the load line in FIG. 33 with the demagnetization curves of the various materials shown indicates that neodymium has the highest energy product at the point of intersection with the load line. This results in part from its high coercivity. Thus, the preferred material is neodymium. However, other materials, such as samarium-cobalt and ferrite, may also be used in the device.

The magnetic bodies in the device of FIG. 2 are preferably center-charged, which means the magnetic energy is concentrated on the central axis of each magnet rather than being distributed uniformly over the face of the magnet. The magnetic induction field over the center-charged face has a steeper gradient than the field over a non-center-charged face. As explained below, the magnitude of the gradient is believed to be a significant factor in the effectiveness of the magnetic device.

Suitable center-charged neodymium magnets are manufactured by Delco Remy, a division of General Motors Corporation, as well as several other sources including the government of the Peoples Republic of China.

Housing 20 holds the magnetic bodies in the desired orientation. Housing 20 may comprise a thermoplastic plastic mass in which the four magnetic bodies 12, 14, 16, and 18 are embedded. Housing 20 may alternatively comprise a thin woven sheath.

Figure 6:
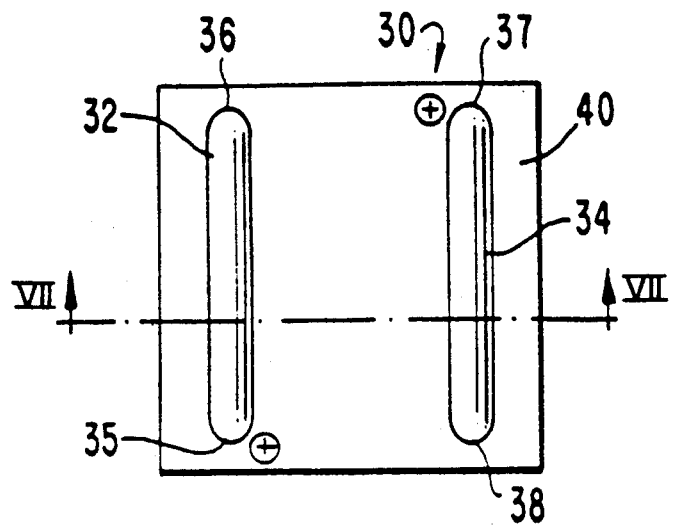
FIG. 6 is a plan view of a second embodiment of a magnetic device in accordance with the principles of the invention.
Figure 7:
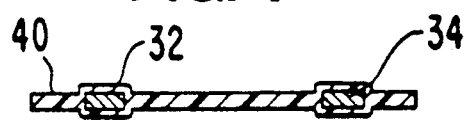
FIG. 7 is a cross-sectional view taken along the line VI—VI of FIG. 6.

A second embodiment of the permanent magnet device, as shown in FIG. 6, comprises two flat, elongated permanent magnets 32 and 34, each having a positive pole and a negative pole. As shown in FIG. 7, elongated magnet bodies 32 and 34 are embedded in a containment body 40 comprised of a plastic material. The magnets form a quadrapolar arrangement. Positive pole 35 and negative pole 36 of magnetic body 32 and positive pole 37 and negative pole 38 of magnetic body 34 are oriented to define the four vertices of a rectangular shape in which positive poles 35 and 37 define opposite diagonal vertices of the rectangular shape and negative poles 36 and 38 define opposite diagonal vertices of the rectangular shape.

The magnetic field generated by the first embodiment, permanent magnetic device 10, is illustrated and quantified in the graphs and charts of FIGS. 8-17. The measurements in FIGS. 9-16 were made with a Hall-effect probe and a Gauss meter on an octapolar permanent magnetic device as shown in FIG. 2, in which each of the four magnetic bodies was a neodymium magnet, having a diameter of 0.5" (1.27 cm) and an energy product of 27 MG-Oe. The interpole distance (from the center of one magnet's face to that of an adjacent magnet) is 14 mm.

This octapolar arrangement of center-charged neodymium magnets produces a focused magnetic field with a steep gradient, that is, a large change in the magnitude of the magnetic field with respect to distance, over a relatively large area.

Figure 8:
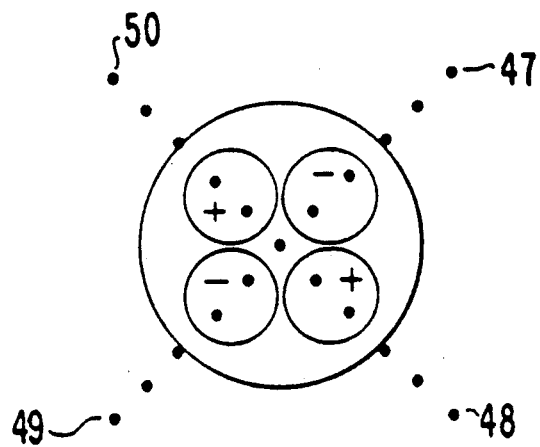
FIG. 8 is a top view of the magnetic device of FIG. 2, with dots added to designate magnetic field measurement locations.
Figure 9:
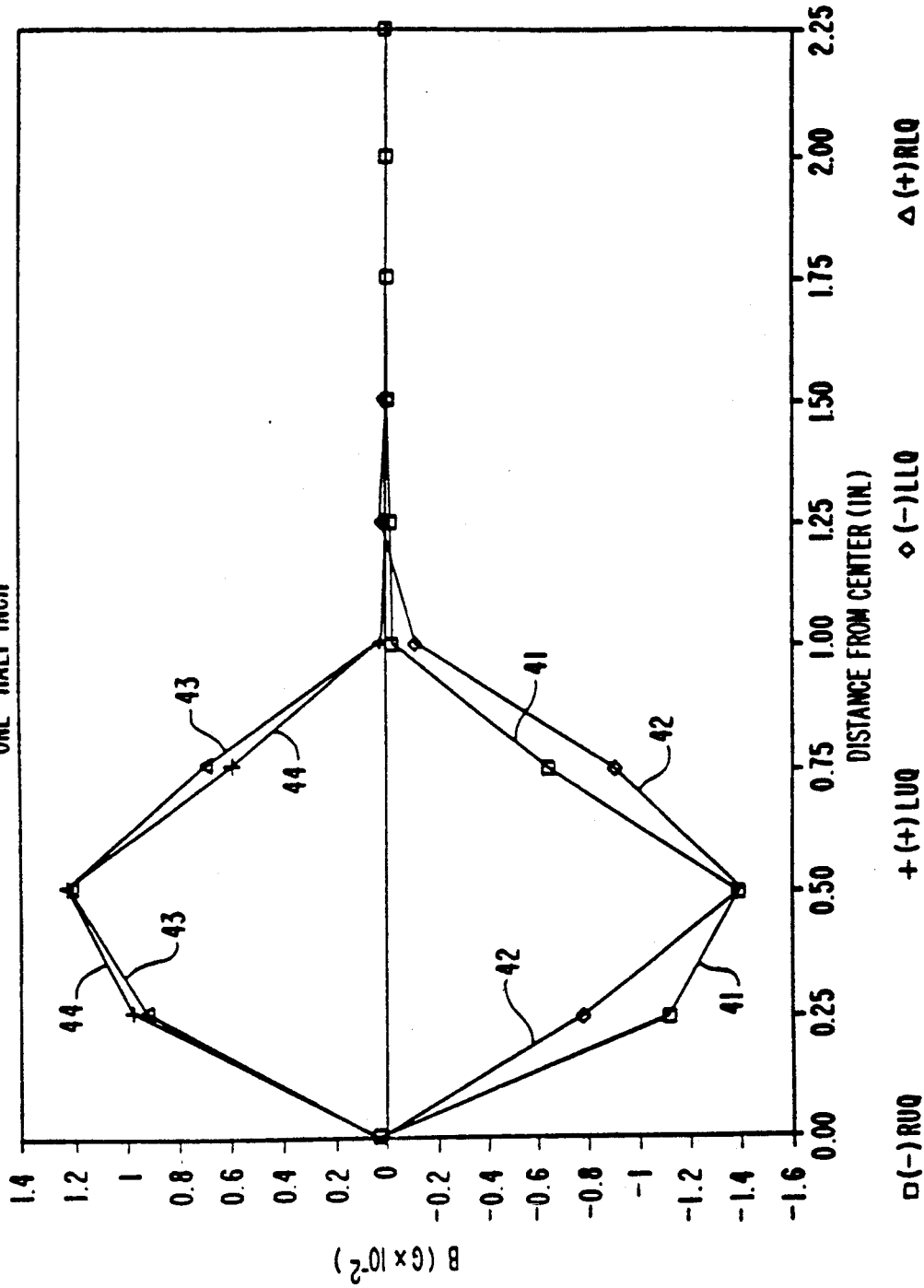
FIG. 9 is a graph of magnetic field measurements taken at the measurement locations designated in FIG. 8.

FIG. 9 is a graph of magnetic field measurements taken along the surface of the magnetic device at measurement locations spaced 0.25" (0.63 cm) apart along the diagonal lines shown in FIG. 8. The measurements are of the component of the magnetic induction perpendicular to the plane of the device. Graph line 41 in FIG. 9 corresponds to measurements taken along the diagonal 46-47 in FIG. 8; graph line 42 corresponds to measurements taken along the diagonal 46-49; graph line 43 corresponds to measurements taken along diagonal 46-48; and graph line 44 corresponds to measurements taken along the diagonal 46-50.

The data in FIG. 9 illustrate that the magnitude of the magnetic field is negligible at the center of the magnetic treatment device, is greatest at 0.5" (1.27 cm) from the center of the device (i.e., near or at the center of the face of a magnet) in each of the four diagonal directions and decreases to almost zero at 1.25" (3.17 cm) from the center of the device. The octapolar arrangement of the device creates a magnetic field coning effect in which the magnetic field is negligible at the center of the device and is greatest at approximately 0.5" (1.27 cm) from the center of the device, with steep gradients in all directions from the center over a relatively large area.

FIGS. 10-16 show data from magnetic field measurements taken at various distances from the surface of the magnetic device described with regard to FIGS. 8 and 9. The location on the faces of the magnets (i.e., the center of their faces) of the positive poles are designated by the letter "N" (north) and of the negative poles are designated by the letter "S" (south). The measurements were taken at the distances from the surface of the magnetic device given in the following table:

| Fig. # | Distance from surface (in./cm) |
|---|---|
| 10 | 0.0/0.0 |
| 11 | 0.4/1.02 |
| 12 | 0.8/2.03 |
| 13 | 1.2/3.05 |
| 14 | 1.6/4.06 |
| 15 | 2.0/5.08 |
| 16 | 2.75/6.99 |

The measurement grids of FIGS. 10-16 are each 6.0" by 6.0" (15.2 cm by 15.2 cm) with individual grid squares of 0.5" by 0.5" (1.27 cm by 1.27 cm). The Gauss meter was used to measure the magnetic field at the center of each grid square and the measurement was recorded on the corresponding grid square of FIGS. 10-16. Again, the measurements are of the component of the magnetic induction perpendicular to the plane of the device.

As can be seen from this data, measurable magnetic induction extended out two inches from the surface of the device. At 2.75" (6.99 cm) above the surface of the treatment device, the measuring device used in the test was not sensitive enough to quantify the intensity of the magnetic field, but was able to distinguish between a positive (north pole) and negative (south pole) field, as shown in FIG. 15. Thus, it can be seen that a detectable octapolar magnetic field extends out at least as far as 2.75" (6.99 cm) from the surface of the magnetic device of the present invention. A significant biological effect on neurons has been observed when the neuron was at a distance from the device such that the field strength at the neuron was 50 G (approximately 2 cm). Further, it is believed that a biological effect takes place at field strengths of less than 1 G, provided that the neuron is symetrically surrounded by the octapolar field of the device. As explained below, it is believed that the magnitude of the magnetic induction is not the only factor—it is the combination of the magnitude and the gradient.

Figure 18A:
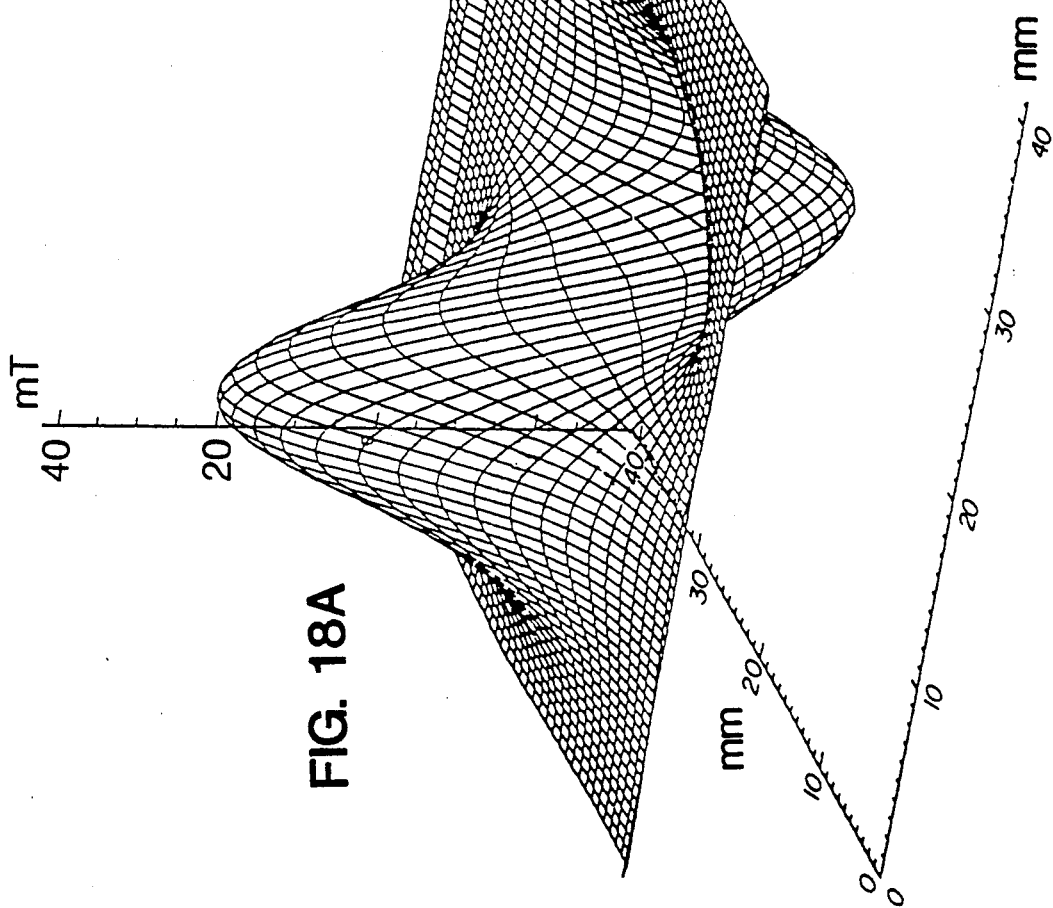
FIGS. 18A-B are an illustration of the magnetic field of another magnetic device and an illustration of that device, respectively.

FIG. 17A depicts the magnetic field generated by magnetic device 10 (shown again in FIG. 17B for reference). The measurements were measured at a distance of 3 mm from the surface of the magnetic device in the same way as the measurements for the data in FIGS. 9-16, and are shown in milliTesla (mT). FIG. 18A depicts the magnetic field generated by a magnetic device having two of the magnets of the device of FIG. 2 (the two-magnet device being shown schematically in FIG. 18B for reference).

FIGS. 18A and 17A illustrate the effect that the proximity of the magnets to each other has on the magnetic field produced by the devices. First, as the artisan would recognize, placing magnets of opposite polarity near to each other reduces the peak magnitude of the magnetic induction over each magnet, since the magnetic field produced by one magnet offsets the field produced by one of opposite polarity. Second, the magnetic induction has a steeper gradient between adjacent magnets of opposite polarity than does the induction on the distal side of each magnet or about an isolated magnet.

Figure 18B:
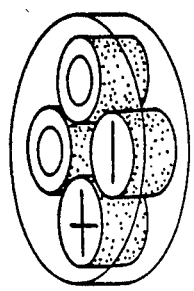

Third, in adding two more magnets to the device shown in FIG. 18B (thus producing the octapolar arrangement of FIGS. 2 and 17B), the peak magnitude of the magnetic induction is further reduced. For example, a comparison of FIG. 17A to FIG. 18A indicates that the peak induction is reduced from approximately 20 mT (200 G) to 10 mT (100 G). Adding more magnets of opposite polarity about the four magnets of the device of FIG. 2, would further reduce the peak induction.

Fourth, the additional two magnets in the device of FIGS. 2 and 17B produce a larger region in which the magnitude of the magnetic induction gradient is large. Although the magnitude of the gradient between the two magnets of the device shown in FIG. 18B is greater than in the region between the four magnets of the device of FIG. 2, the gradient has the larger magnitude over a much smaller region. As explained in detail below, the effect that the device of FIG. 2 has on neurons is believed to stem from the magnitude and extend of the magnetic induction gradient, alone or in combination with the magnitude of the induction itself.

Finally, the artisan will recognize that the effects noted above are related to the proximity of the magnets to each other. The greater the relative distance between the magnets, the more each magnet will behave as though it were isolated from the magnetic fields of the other magnets. Correspondingly, the closer the magnets are placed to each other, the greater the magnitude of the gradient of the magnetic induction. The effect of distance is quite pronounced since the strength of the magnetic field about the thin magnets of the device of FIG. 2 (which can be approximated as magnetic dipoles) decreases with the cube of the distance from the magnet.

It is thus preferred to place the magnets as close to each other as possible. However, the magnets should at least be placed within a distance from each other in which the magnitude of the magnetic induction produced by each magnet is a significant percentage of its peak value at the locations of the other magnets. From the data shown in FIGS. 9-18, it can be seen that for neodymium magnets, the magnitude of the magnetic induction reaches a small percentage of its peak value at a distance of approximately two diameters (1.0"/2.54 cm) from the center of each magnet.

EFFECT OF MAGNETIC DEVICES ON NEURONS

The method by which the magnetic device 10 is used to block depolarization of neuron membranes is described below. The device of FIG. 2 was tested, as well as several other configurations of magnetic bodies. The data show that the device of FIG. 10 produces better blocking of neuron membrane depolarization than any of the other tested configurations. The testing methodology is described below, then the test results are presented.

NEURON PREPARATION AND TESTING

Cultures of spinal cord neurons were prepared according to the following procedure. Spinal cords and attached dorsal root ganglia were dissected from fetal (12-14 days gestation) mouse embryos. The tissue was minced and then mechanically dissociated by trituration in $Ca^{++}$ and $Mg^{++}$ free balanced salt solution to a suspension of single cells and small clumps. The disassociated cells were then suspended in culture medium. The culture medium consisted of 50% Eagle's Essential Medium and 50% Hank's balanced salt solution, supplemented with: 1.5 g of dextrose; and 0.75 g of $NaHCO_3$/500 ml, 5 ml % (5 ml per 100 gm) heat-inactivated horse serum; 5 ml % fetal calf serum; 1 ml % Nu-Serum; and 10 ng/ml of nerve growth factor. The cells and medium were then placed in sterile collagen-coated 35 mm dishes. The cultures were maintained in an incubator with an atmosphere of 90% room air and 10% $CO_2$ at 35° C. A bicarbonate/$CO_2$ buffer maintained the cultures pH at 7.4. Growth of rapidly dividing non-neuronal cells was suppressed by adding 0.5 µg/ml of fluorodeoxyuridine for 1-2 days after one week in vitro. After treatment with the uridine analog, the fetal calf serum was excluded. Thereafter, the medium was changed twice weekly. Cultures were maintained for up to six months before electrophysiological tests.

The test apparatus is shown in FIG. 1. With the assistance of a micromanipulator 31 (such as Leitz micromanipulators) a microelectrode 15 is inserted into the neuron 13 in a culture dish 11. Microelectrode 15 is a glass pipette with a fine tip having a microscopic opening through which both electric stimuli may be applied and electric potentials may be measured. The microelectrode is filled with 3M potassium acetate. Dish 11 contains a perfused heated bath for supporting neuron 13. An electric pulse generator 21 is connected to microelectrode 15 through a headstage amplifier 19 and a bridge amplifier 27 such that sensory neuron 13 may be subjected to electric pulses produced by electric pulse generator 21. A ground electrode 25 is placed in the bath in dish 11.

Ground electrode 25 is electrically connected to headstage amplifier 19 such that electric potentials across the membrane of neuron 13 may be measured. Bridge amplifier 27 is connected to an oscilloscope 17 both directly and through differentiator 28. Oscilloscope 17 displays changes in the electrical potential of cell 13 as sensed by microelectrode 15 and ground electrode 25. A recording device including, for example, a digital processor 29 and a video recorder 23 may be connected to bridge amplifier 27 in order to generate a record of the electrical behavior of nerve cell 13. The magnetic device to be tested is positioned below neuron 13.

For test purposes, the culture medium in the culture dish was exchanged for a modified Dublbecco's phosphate-buffered saline. The composition of this station was: in millimolar: NaCl, 143.4; KCl, 4.2; CaCl$_2$, 0.80; MgCl$_2$, 3.0; and glucose, 11.0 in 9.5 mM sodium-phosphate buffer at pH 7.4. The culture dish was then placed on an aluminum block heated by a Peltier device with temperature regulated to 37° C. The dish and block were mounted on the stage of a Leitz inverted microscope fitted with phase contrast optics to facilitate placement of the microelectrode. Under direct visual control, the microelectrode was inserted into a nerve cell in the culture dish using micromanipulators 31.

A stimulating electric current was applied to the impinged nerve cell through the micropipette. Use of an active bridge amplifier 27 (Dagan 8100 Axon instrument clamp or W-P instruments M707) and a second ground electrode 25 in the culture dish solution permitted simultaneous application of the stimulating current and recording of the electric potential difference across the membrane of the cell under study.

The potential differences across the cell membrane were digitized with an audio processor 29 and then recorded on videotape by recorder 23. The potential differences were also photographed from a Tektronic R5113 oscilloscope with a Grass oscilloscope camera.

Using the cell culture and testing arrangement described above, small (0.5-1.0 nA) current pulses were applied to the nerve cell approximately every 2.0 s. For several minutes, control measurements were recorded with no magnetic device present. Each time an electric pulse was applied to the nerve cell interior, the recording apparatus recorded a first peak representing the stimulus for inducing cell membrane depolarization. The first peak was quickly followed by a second peak which corresponds to a cell membrane depolarization wave (action potential) that occurs when the applied electric pulse causes the spontaneous formation of sodium currents in the cell membrane. Such depolarization is part of a peripheral nerve cell's pain impulse transmission function. When a cell membrane fails to fire an action potential upon depolarization, the nerve cell does not transmit action potentials and does not stimulate neurons in the central nervous system. Thus, pain is not detected.

Before beginning tests on live cells, the recording apparatus was tested by placing the magnetic device of FIG. 2 1 cm above a culture dish holding culture medium (but no nerve cell) into which the microelectrode and ground electrode were placed. The recording instruments were monitored for ten minutes after the magnetic device was introduced. The introduction of the magnetic device had no effect on the bridge balance, on the microelectrode tip potential, or on the associated electric potential recording apparatus.

SINGLE-NEURON COMPARATIVE TEST DATA

A series of tests were conducted with a single neuron. The effect of several different magnetic devices on the neuron was evaluated. The tests were conducted in three phases. First, control tests were performed in the absence of the magnetic device. Then the magnetic device was put in place and additional tests conducted. Finally, the magnetic device was removed and further tests conducted during a "recovery" period.

The first tests were conducted with the magnetic device shown in FIG. 2. FIGS. 19A to 19E show oscilloscope traces for the neuron's output before application of the magnetic device of FIG. 2.

Each oscilloscope photograph includes a lower line representing the difference in electric potential across the cell membrane and an upper line, calculated by integrator 28, that represents the first derivative of the bottom line. The peak of the differential line represented the maximal rate of rise of cell action potential and was used as a qualitative assay of cell sodium currents generating the upstroke of the action potential.

Figures 19B, 19C, 19D, 19E:
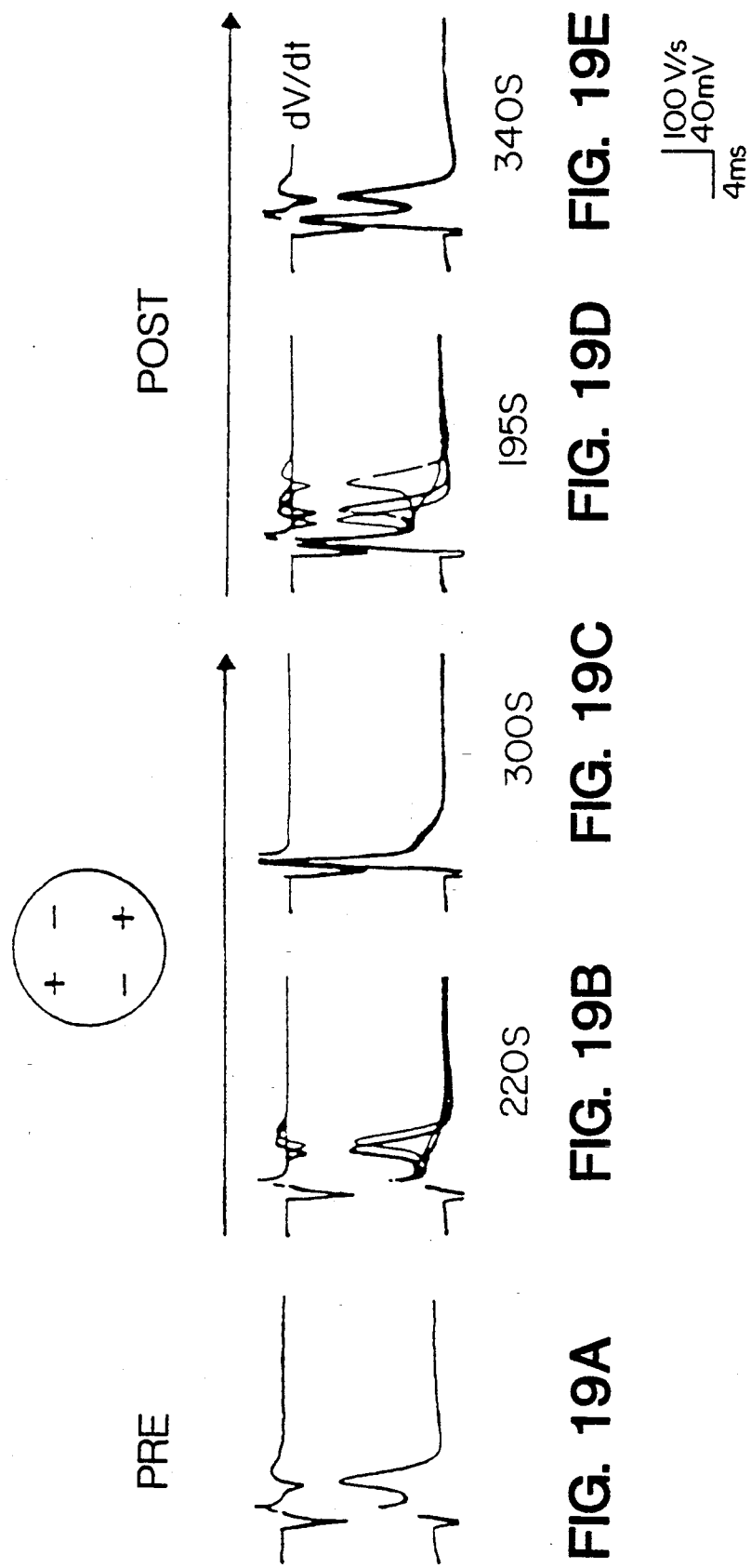
Figures 19F, 19G:
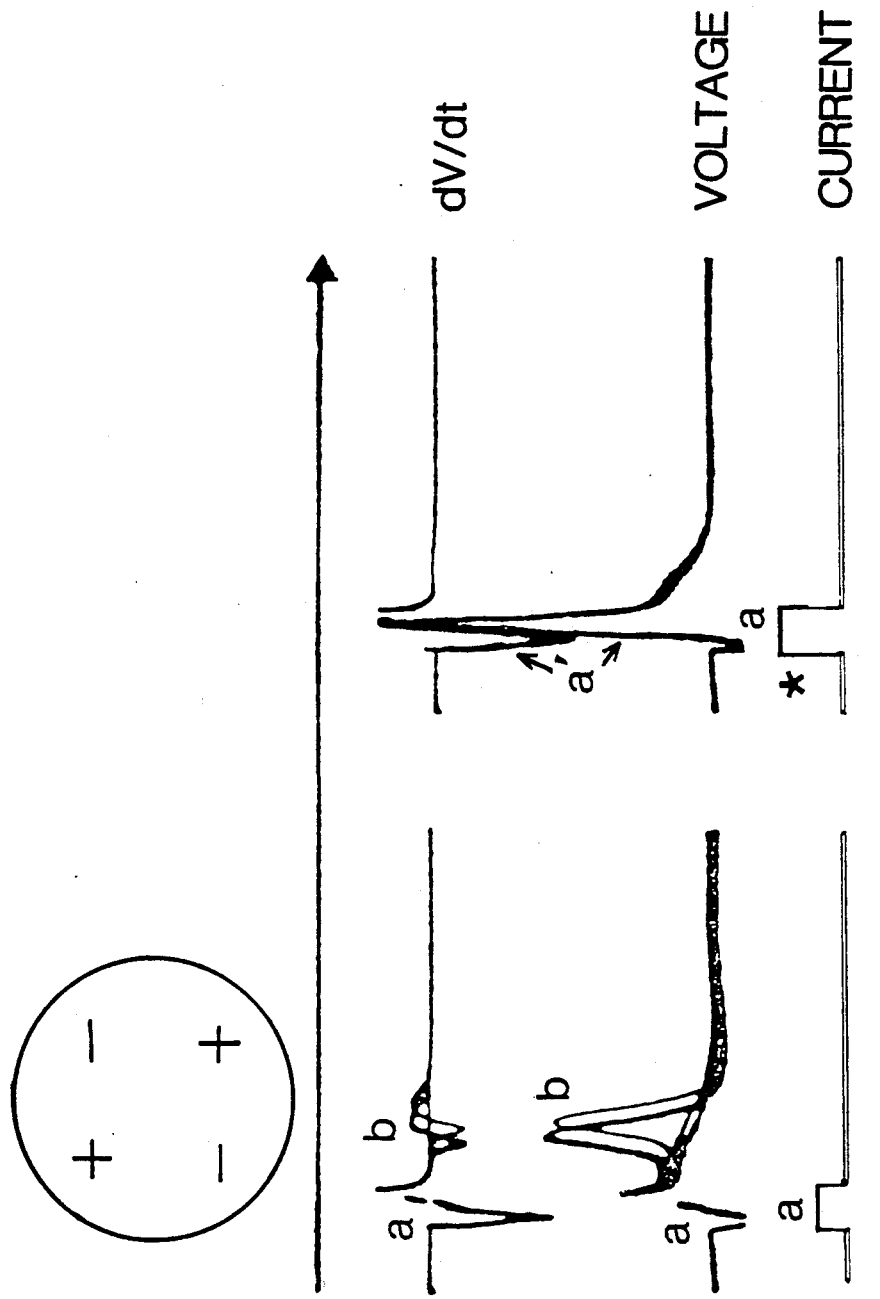

After several minutes, the magnetic device shown in FIG. 2 was positioned 1 cm below the surface of the cell culture fluid above the same impaled nerve cell under study. After the magnetic device was in place approximately 220 s, the nerve cell began not to depolarize with each application of the 0.5 nA pulses. FIG. 19B and (in enlarged scale) FIG. 19F show the oscilloscope output 220 s after application of the magnetic device. In addition to the voltage and dV/dt traces shown in FIGS. 19A to 19D, FIGS. 19F and 19G show, as the bottom trace, the current applied to the neuron.

In each trace, peak "a" corresponds to the application of the 0.5 nA pulse. Peak "a" is followed by a reversal in electric potential differences across the cell membrane that corresponds to the second peak or action potential. Peak "b" represents a change in cell membrane potential from approximately −60 mV to approximately +30 mV. The sloped line under peak "b" represents non-propagated local response and shows that the impinged cell had stopped firing action potentials with each applied electric pulse.

FIG. 19C and (in enlarged scale) FIG. 19G show the oscilloscope output 250 s after application of the magnetic device, by which time action potentials were not elicited by the electric pulses. The complete absence of a second peak shows that action potential firings were blocked. When the voltage of the stimulator pulses was increased to 1.0 nA, action potentials remained blocked.

After the magnetic device was removed, application of the larger 1.0 nA current pulses to the impinged cell was continued. For a little over 180 s the second peak did not appear. FIG. 19D shows the oscilloscope output 195 s after removal of the magnetic device at which time the appearance of an occasional second peak provided evidence of recovery of the ability to fire action potentials. The fully developed second peak of FIG. 19E shows that by 340 s after removal of the magnetic device, the cell fired an action potential with each applied pulse.

The procedure described above for testing the magnetic device of FIG. 2 was repeated on the same nerve cell tested with that device, except that the device was replaced with several different devices, having one, two, or four magnets in various orientations.

Figures 20A, 20B:
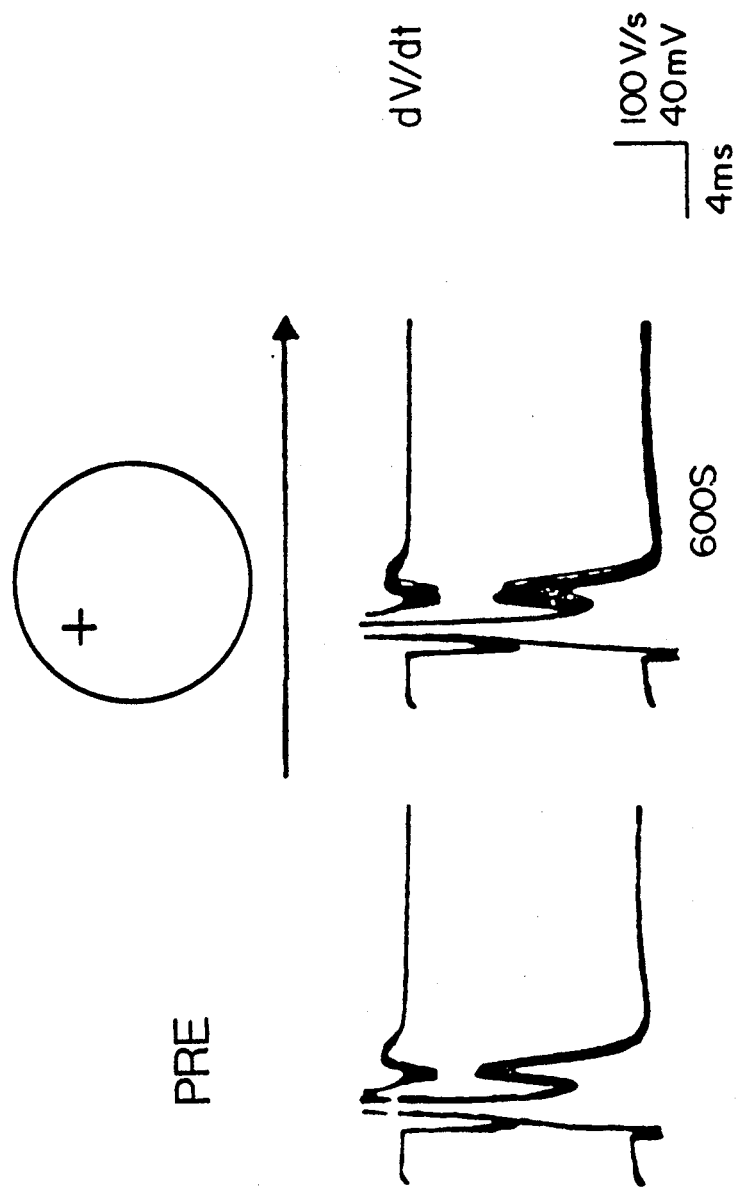

The first alternate configuration tested had one single 0.5" (1.27 cm) diameter neodymium magnet with an energy product of 27 MG-Oe and three 0.5" (1.27 cm) diameter non-magnetic metal bodies. The magnet was oriented with the positive magnetic pole closest to the neuron. FIGS. 20A and 20B show the oscilloscope output both before (FIG. 20-A) and 600 s after (FIG. 20B) the single-magnet device was placed by the nerve cell. As can be seen from the presence of peak "b" in FIG. 20B, this device did not alter nerve cell firing of action potentials.

Figures 21A, 21B:
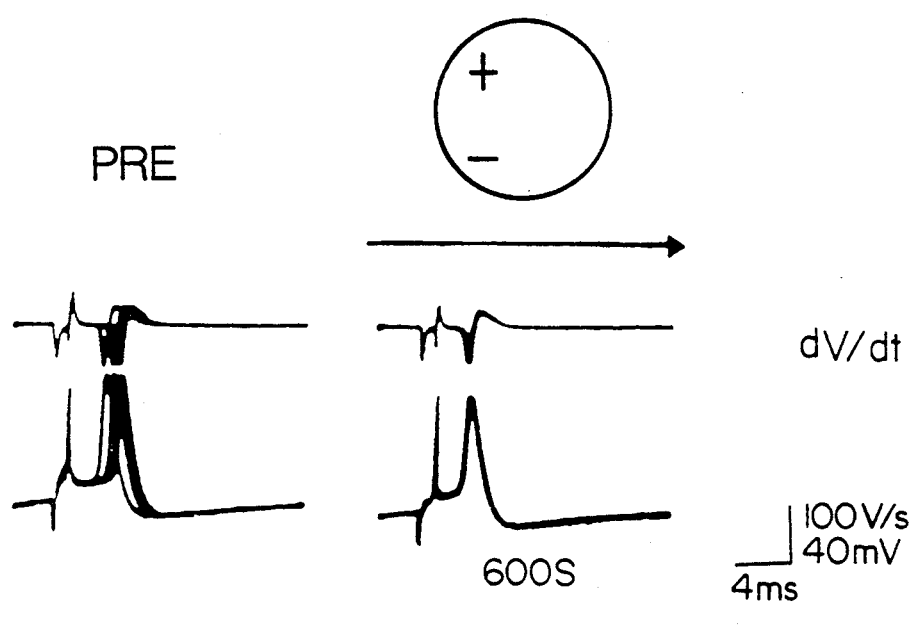

The second alternate configuration had two of the neodymium magnets, arranged with one positive pole facing up, and one pole facing down. FIGS. 21A and 21B show the oscilloscope output both before (FIG. 21A) and 600 s after (FIG. 21B) the device was placed by the neuron. As can be seen by the presence of peak "b," the extent of action potential firing was the same with and without the two-magnet device.

As discussed above, the magnetic field generated by this device at a distance of 3 mm from the top plane of the magnets is shown in FIG. 18B, with the device shown schematically in FIG. 18B.

Figures 22A, 22B, 22C, 22D:
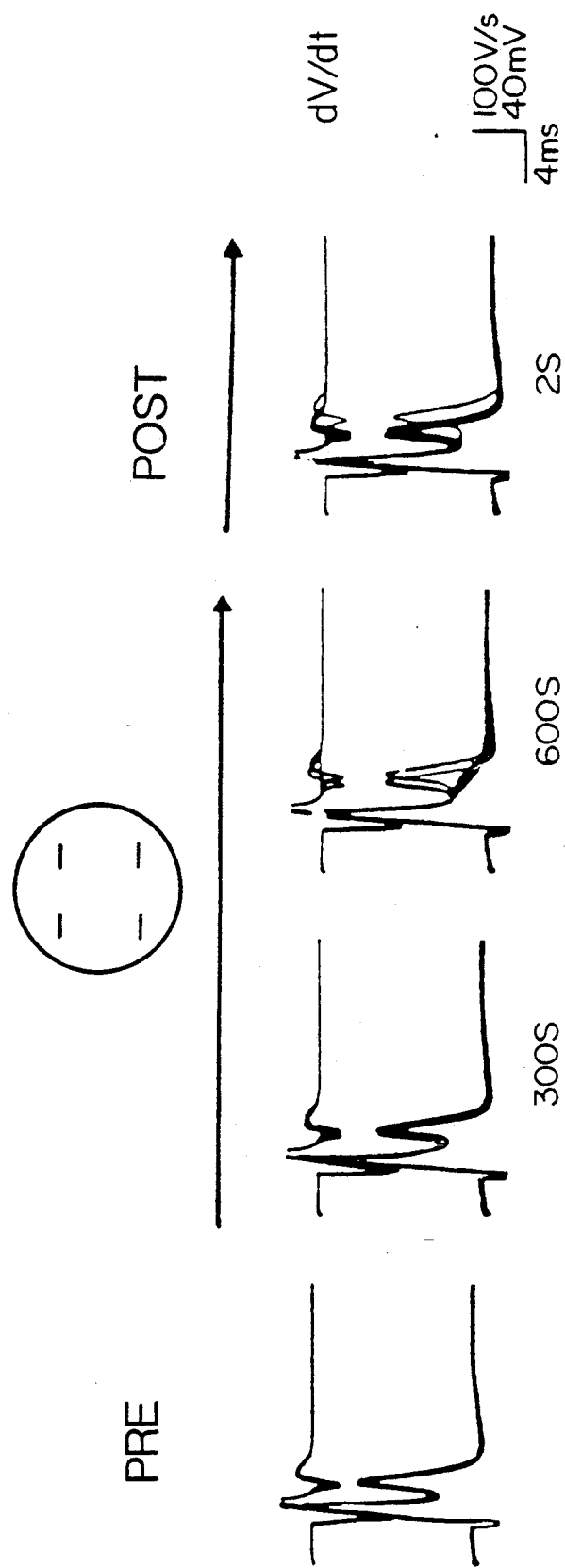

The third alternative device had four magnets arranged with their poles all oriented in the same direction, with all negative poles facing the neuron. FIGS. 22A to 22D show the oscilloscope output before, during, and after the application of the magnetic device. Firing of action potentials was unchanged from before this magnetic device was applied (FIG. 22A) to 300 s after it was applied (FIG. 22B). Even 600 s after the magnetic device was put in place (FIG. 22C), action potential firing was not completely blocked. Firing of action potentials completely resumed immediately upon removal of the device (FIG. 22D). In several other neurons, exposure to the array of four magnets of negative polarity was associated with complete blocking of action potential which returned completely after removal of the device.

The fourth alternate device used four magnets, as in the third device, but with the opposite polarity. FIGS. 23A to 23D show the oscilloscope output before, during, and after the application the fourth device. Firing of action potentials evident before application of the device (FIG. 23A) was reduced within 195 s of application (FIG. 23B) and was eliminated within 270 s (FIG. 23C). However, firing of action potentials resumed immediately upon removal of the magnetic device (FIG. 23D).

MULTIPLE NEURON TESTING

The next series of tests followed the same procedure described above, but compared the efficacy of different magnetic devices as applied to multiple neurons. First, 135 neurons were tested with the magnetic device shown in FIG. 2. In each instance, the voltage of the stimulating current pulse was set just above the threshold level at which all stimuli elicited action potentials. These brief depolarizing current pulses elicited single action potentials lasting between 0.5 and 1.5 ms. (short duration) in 70 of the neurons and single action potentials from 2 ms to 3 ms (long duration) in the remaining 65 neurons. After 420 s exposure to the magnetic device shown in FIG. 2, all stimuli failed to elicit action potentials in 83% of the short duration neurons and in 92% of the long duration neurons. Within 180 to 720 s following removal of the magnetic array, all stimuli elicited action potentials in 43% of the short duration neurons and in 48% of the long duration neurons, while increased current pulses of 10–15 mV elicited action potentials in another 40% of the short duration neurons and 40% of the long duration neurons. Nine of the short duration neurons and nine of the long duration neurons died before recovery was complete.

The same procedure described above was repeated with the device having four magnets with their positive poles oriented toward the neurons (the same device for which single-neuron test results are shown in FIGS. 23A to 23C). The stimuli were applied to 4 short duration neurons and 3 long duration neurons. Application of the device with 4 positive magnetic poles for up to 300 s blocked firing of action potentials in all 7 neurons. Upon removal of the magnetic device, full recovery of action potential firings occurred within seconds in all 7 neurons.

The procedure was repeated for a device with four negative poles oriented toward the neuron (the same device for which single-neuron test results are shown in FIGS. 22A to 22D). The device was applied to 4 short duration neurons and 3 long duration neurons. In 3 of the 4 short duration neurons, application of the device with 4 negative poles for up to 600 s completely blocked firing of action potentials. In the fourth short duration neuron, the device blocked only 50% of action potentials. The same application of the device completely blocked action potentials in one of the long duration neurons and blocked approximately 50% of action potentials in the other 2 long duration neurons. Upon removal of the magnetic device, full recovery of action potential firings occurred within seconds in all 8 neurons.

PULSED-STIMULATION MULTIPLE NEURON TESTING

In an effort to quantify the effect on nerve cells of the method of the present invention, 27 short duration neurons were prepared according to the procedure described above, then tested according to the following procedure. First, 50 identical electric stimuli pulses were applied to each impaled neuron at a frequency of 1 pulse/s during two 50 s control periods during which no magnetic devices were near the neuron being tested. The voltage of the stimulating current pulse was set just above the threshold level at which essentially all stimuli elicited action potentials. The number of times the cell failed to elicit a responsive action potential was recorded and used as a baseline failure rate.

After the baseline recording was taken, the magnetic device shown in FIG. 2 was positioned 0.5 cm below the bottom of the cell culture dish, below the impaled nerve cell. Fifty stimuli pulses, identical to the one pulse/s pulses applied during the control periods, were applied to the impaled neuron under study during each of four consecutive 50 s magnetic exposure test periods. The number of times the neuron failed to elicit a responsive action potential during each of the four 50 s magnetic exposure test periods was recorded.

Following the four 50 s magnetic exposure periods, the magnetic device was removed, and the neuron was subjected to another four consecutive sets of 50 stimuli pulses at a frequency of 1 pulse/s at the same voltage level as applied during the two control periods. The number of times the neuron failed to elicit a responsive action potential during each of the four 50 s recovery test periods was recorded.

Another 21 short duration neurons were tested following the same procedure of two 50 s control test periods, four 50 s magnetic exposure periods, and four 50 s recovery test periods. However, for the second set of 21 neurons, a two-magnet device (the same device for which single-neuron test results are shown in FIGS. 21A and 21B) was applied in place of the magnetic device shown in FIG. 2 during the four magnetic exposure test periods. During the magnetic exposure test periods, the two magnet device was positioned 0.5 cm below the bottom of the cell culture dish, below the impaled nerve cell. The number of times that each neuron studied failed to elicit an action potential in response to any one of the 50 stimuli applied during each of the two control periods, during each of the four magnetic exposure periods and during each of the four recovery periods was recorded.

Figure 24:
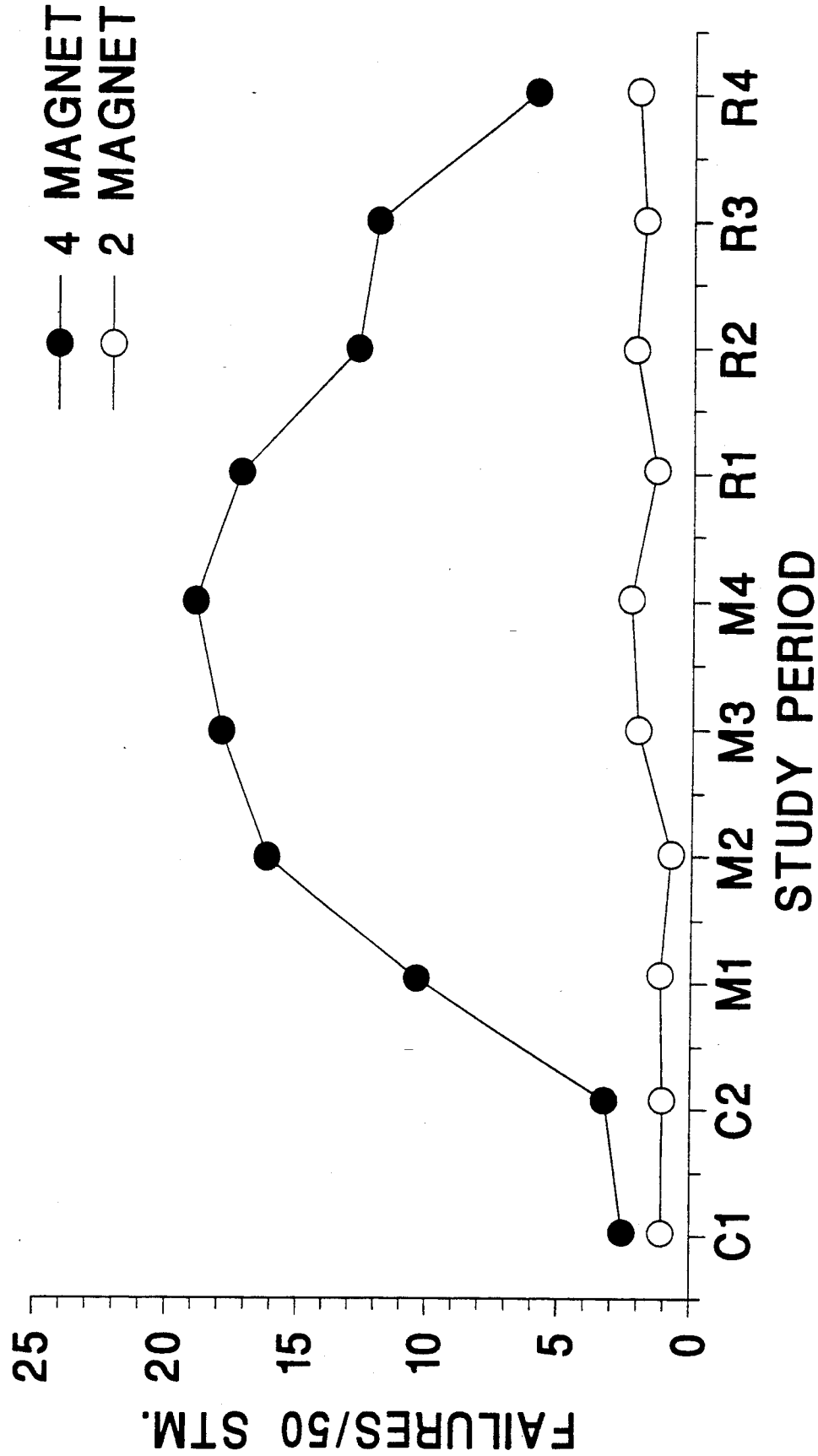
FIG. 24 is a graph comparing the average number of times neurons failed to elicit action potentials in response to applied stimuli before, during, and after exposure to the magnetic device of FIG. 2 and to a two-magnet device.

FIG. 24 shows the average number of times the neurons tested according to the procedures described above failed to elicit action potentials during each of the test periods. Designations "C1" and "C2" are for the two control periods, designations "M1"–"M4" are for the four magnetic exposure periods, and designations "R1"–"R4" are for the four recovery periods. The closed circle data points represent the average number of response failures during each test period for the group of 27 neurons exposed to the magnetic device of FIG. 2 during the magnetic exposure periods. The open circle data points represent the average number of response failures during each test period for the group of 21 neurons exposed to the two magnet device during the magnetic exposure periods. The number of failures during test periods M1–M4 and R1–R3 for the four magnet array was greater than the number of failures for the bipolar array by a statistically significant amount.

Figure 28A:
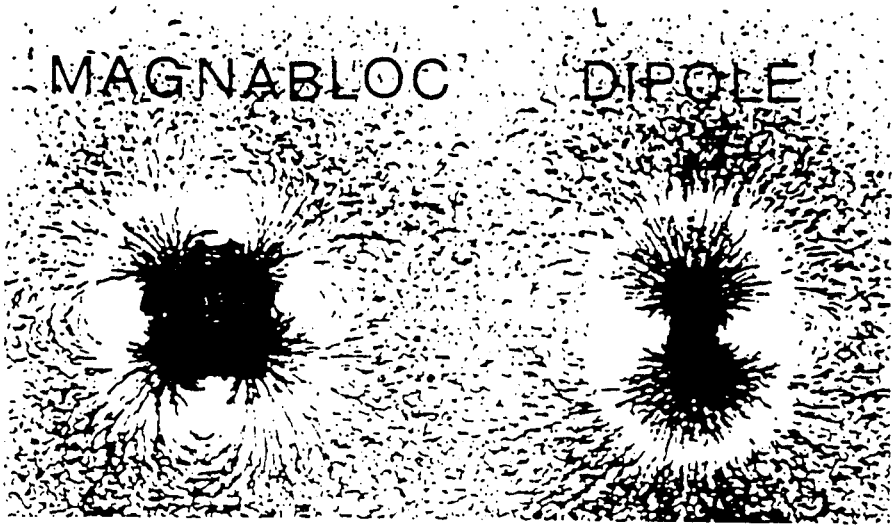
FIGS. 28A–B illustrate the magnetic field around the magnetic device of FIG. 2 and a 2-magnet device, and show comparative neuron firing data for the two devices.
Figure 28B:
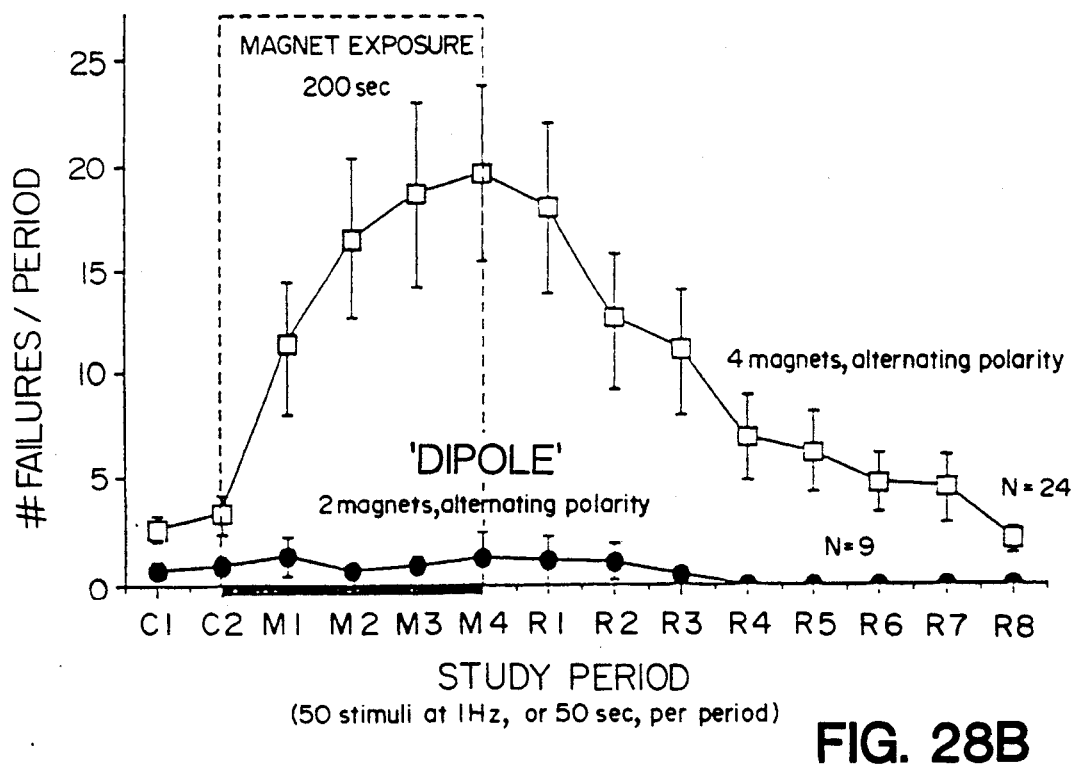

This same procedure was repeated with an additional 24 neurons for the device of FIGS. 2 and 9 neurons for the two-magnet device. The results are shown in FIG. 28B. The magnetic field about the device of FIG. 2 and the two-magnet device is illustrated in FIG. 28A by iron filings.

Figure 25A:
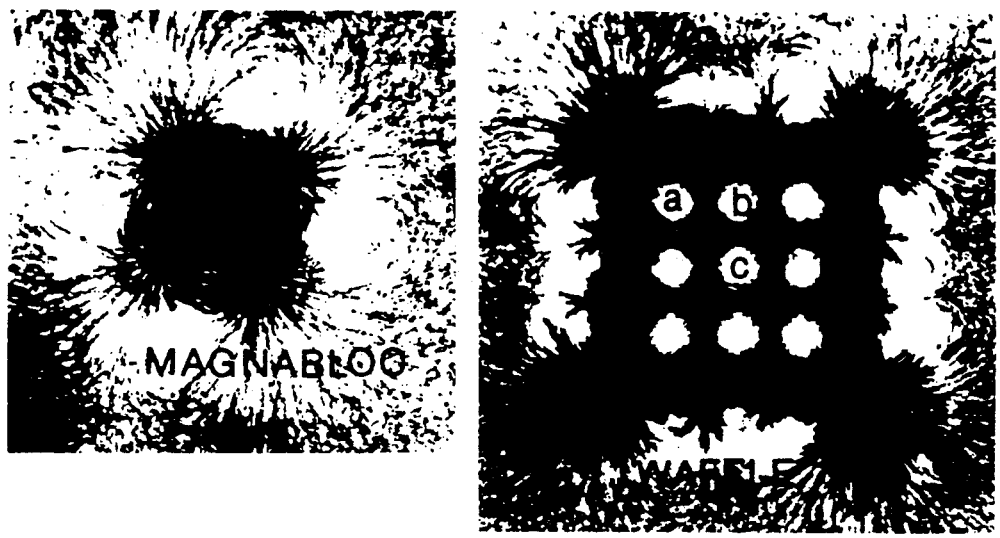
FIGS. 25A–C illustrate the magnetic field around the magnetic device of FIG. 2 and a 16-magnet device, and show comparative neuron firing data for the two devices.
Figure 25C:
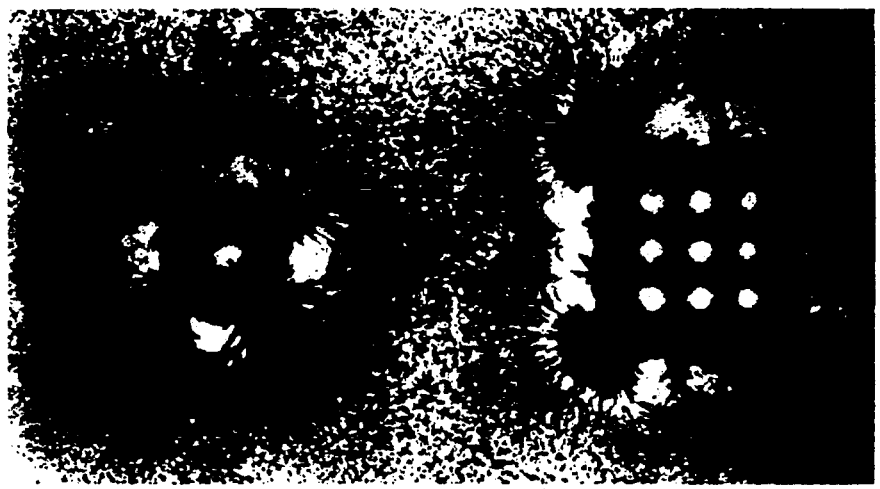
Figure 25B:
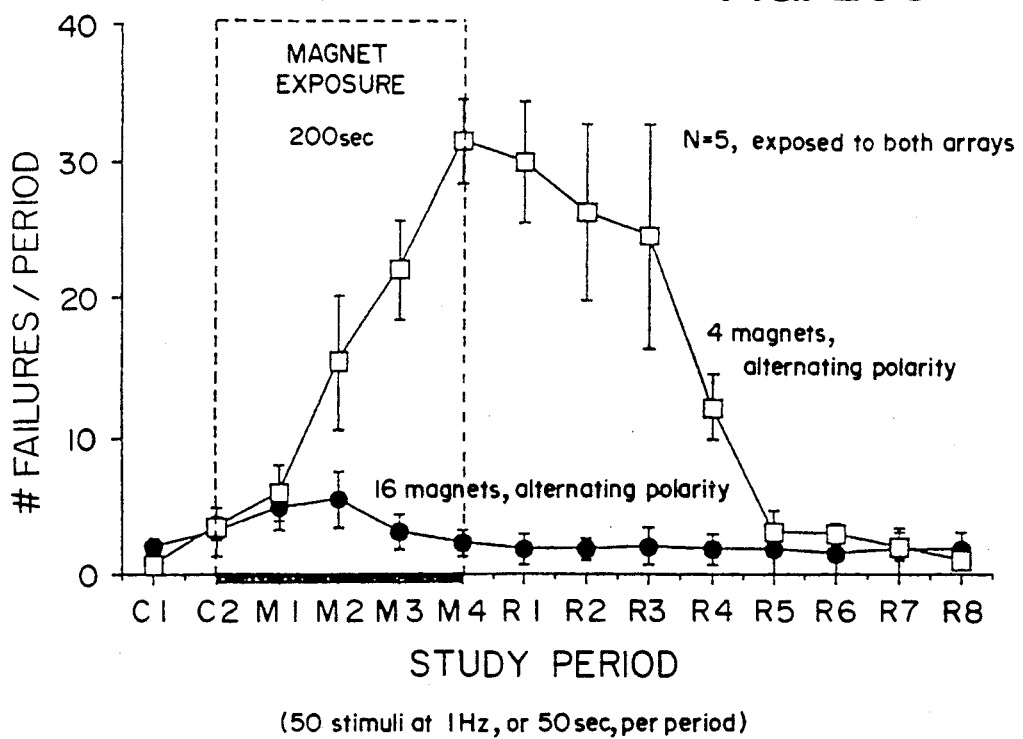

The same procedure was repeated with 5 neurons using the device of FIG. 2 and a 16 magnet device in which the magnets are arranged as though four of the devices of FIG. 2 were placed adjacent one another. FIG. 25A illustrates the magnetic field (as indicated by the distribution of iron filings) over the device of FIG. 2 and the sixteen magnet array. FIG. 25C indicates with white circles the positions of the magnets under the iron filings.

When the device of FIG. 2 was in place for approximately 120 s, the neuron began not to depolarize with each application of the 0.5 nA pulses, with maximum effect noted at between 240 and 300 s. After the device was removed, recovery of the neuron's ability to depolarize with 0.5 nA was noted.

When a sixteen magnet array was applied to the same cell in the same fashion, very different results were obtained. When a sixteen magnet array was exposed to the cell at a distance of 1 cm from the cell in locations (a), (b) and (c) as shown on FIG. 25A (i.e., between the magnets) for the same length of time as the four magnet array was exposed, the rate of depolarization was not altered. The few stimuli that did not result in depolarizations did not yield a result that was statistically different from the baseline.

EFFECT OF MAGNET SPACING

Figure 30:
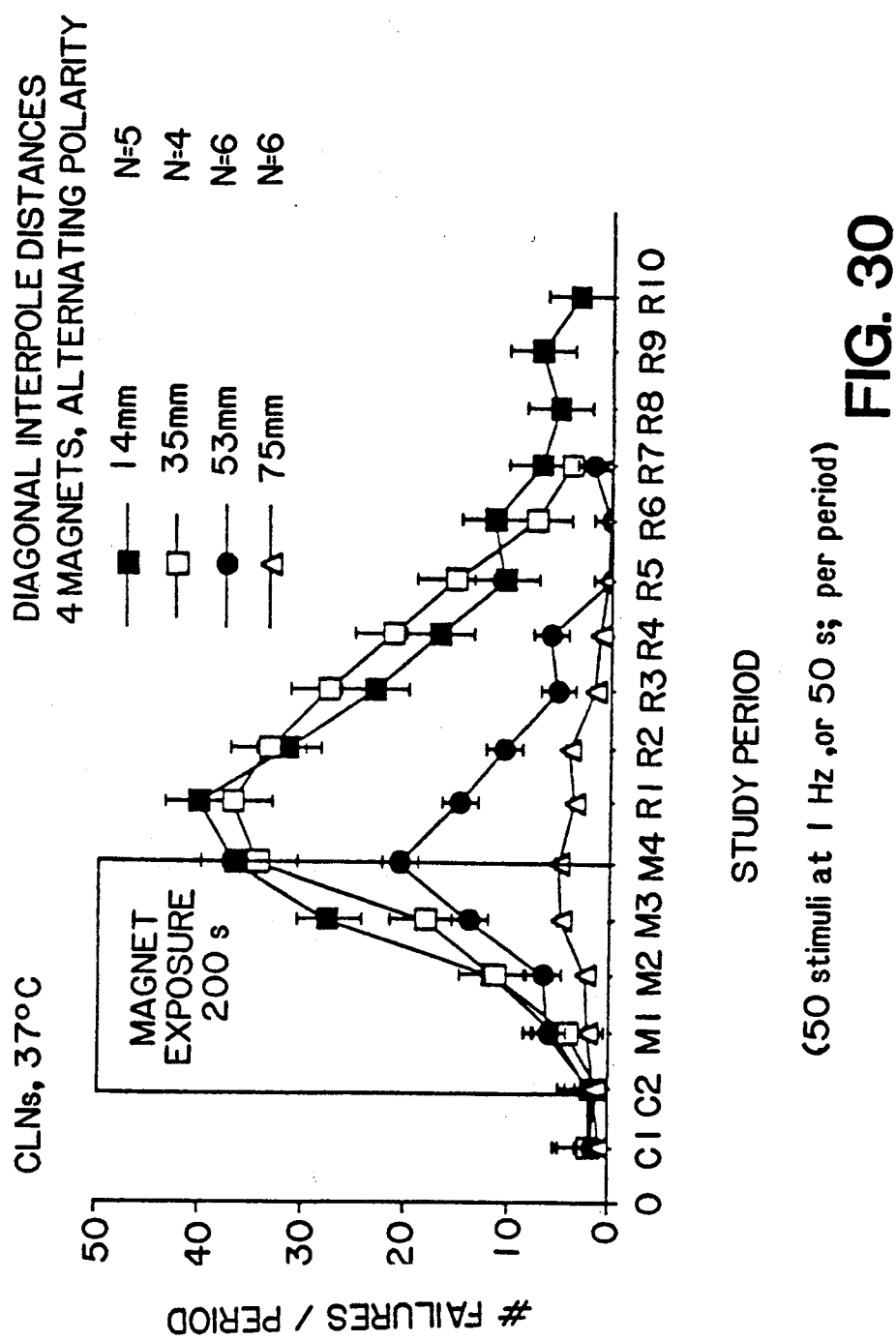
FIG. 30 is a graph comparing the average number of times neurons failed to elicit action potentials in response to applied stimuli before, during, and after exposure to the magnetic device of FIG. 2 and to similar magnetic devices in which the magnets were spaced from each other at various distances.
Figure 31:
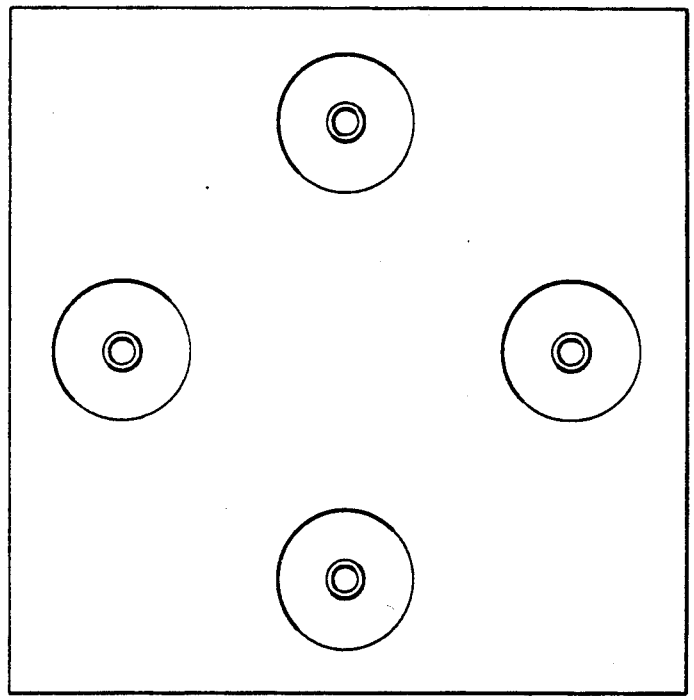
FIG. 31 shows a test fixture in which the magnets were held during the testing for which the data are shown in FIG. 30.

FIG. 30 represents data generated for a single neuron as first described above with a four-magnet device in which the magnets were symmetrically spread at various distances in plastic holders such as shown in illustrated in FIG. 31. Interpole distances of 14 mm, 35 mm, 53 mm, and 75 mm were tested. For the 0.5" (12.7 mm) diameter magnets used, these interpole distances correspond to 1.1, 2.8, 4.2, and 5.9 diameters, respectively. It is evident from the test results that at an interpole distance of 75 mm (5.9 diameters) the device has virtually no biological effect. There is some biologic effect at 53 mm (4.2 diameters) but the effect is truly significant at distances of 35 mm (2.8 diameters) or less. These results are consistent with the discussion above of the effect of magnet proximity on the magnitude of the magnetic induction gradient, i.e., that the magnets should be close enough to each other that the magnetic induction produced by one magnet is significant at the location of the other magnets. Placing thin neodymium magnets within approximately three diameters of each other should achieve the desired effect on neurons.

Figure 26A:
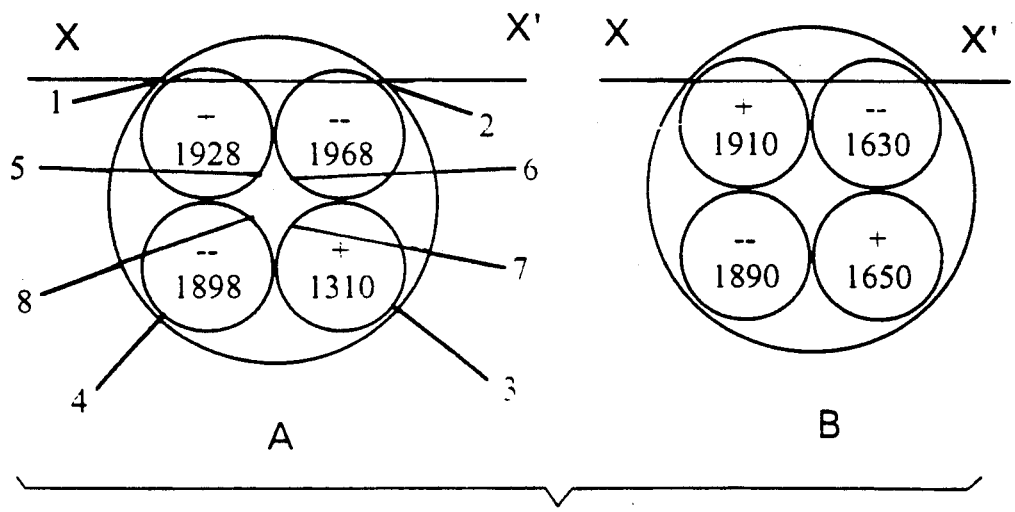
FIGS. 26A–B show the arrangement of two of the magnetic devices of FIG. 2 for measurement of their magnetic fields.
Figure 26B:
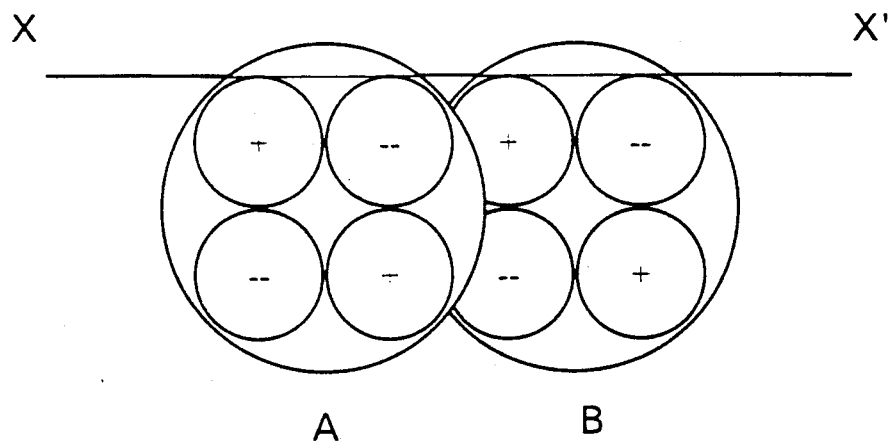
Figure 29:
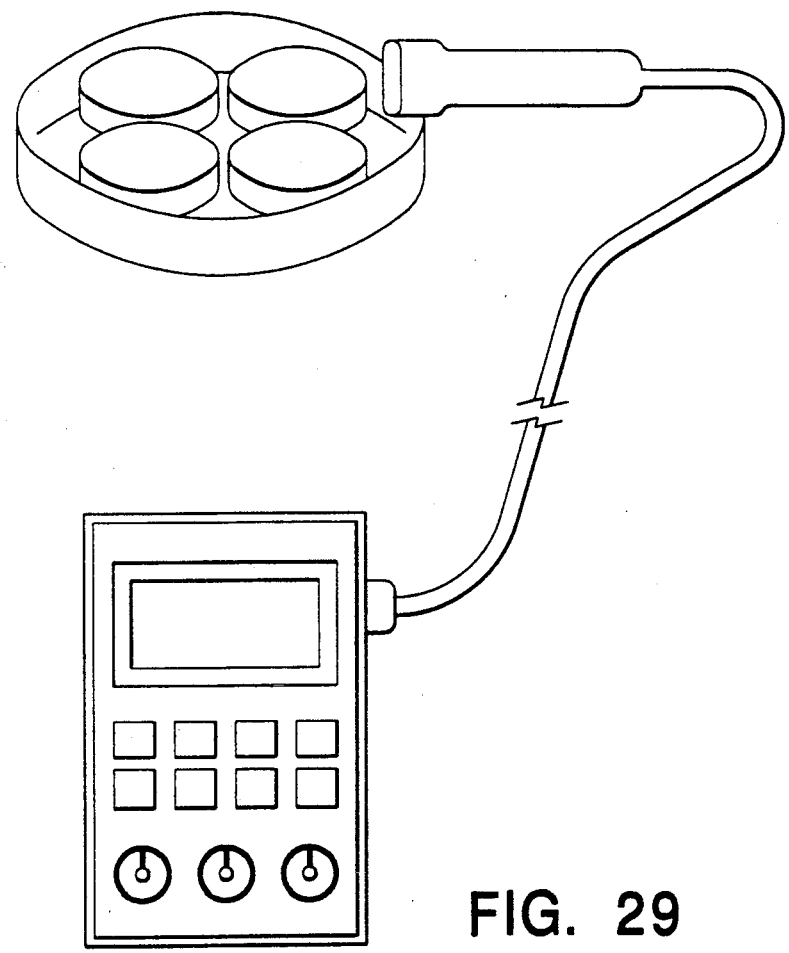
FIG. 29 schematically illustrates the apparatus used to measure the magnetic field data shown in FIG. 27.

Disposing additional poles adjacent to the four magnet device distorts the symmetry of, and reduces the magnitude of, the gradient effect. FIG. 26A shows two four-magnet devices (device A and device B) that were scanned in the horizontal plane, as shown in FIG. 29. The magnitude of the magnetic induction component perpendicular to the devices was measured first with the two devices separated, as illustrated in FIG. 26A. The measurements were made at 8 locations on each device, as indicated on one of the devices shown in FIG. 26A. The two devices were then placed together as illustrated in FIG. 26B, so that they were physically touching, and the magnetic induction measured again at the same 8 points on each device. This data is presented in the following table and is plotted in FIG. 27. The magnitude and polarity of the magnetic induction at the center of each face in the two devices is also shown in FIG. 26A.

| | Separate (Gauss) | | | | Together (Gauss) | | | |
|---|---|---|---|---|---|---|---|---|
| | Device A | | Device B | | Device A | | Device B | |
| Loc. | Mag. | Grad. | Mag. | Grad. | Mag. | Grad. | Mag. | Grad. |
| 1 | 118 | 1810 | 124 | 1786 | 356 | 1572 | 250 | 1660 |
| 2 | −148 | 1820 | −130 | 1500 | −256 | 1312 | −418 | 1212 |
| 3 | 218 | 1098 | 180 | 1470 | 250 | 1060 | 389 | 1261 |
| 4 | −189 | 1709 | −160 | 1730 | −418 | 1480 | −252 | 1618 |
| Avg | 168 | 1609 | 148 | 1621 | 320 | 1356 | 327 | 1437 |
| 5 | 238 | 1690 | 250 | 1660 | 469 | 1459 | 313 | 1597 |
| 6 | −256 | 1712 | −260 | 1370 | −277 | 1691 | −416 | 1214 |
| 7 | 369 | 941 | 240 | 1460 | 401 | 909 | 403 | 1247 |
| 8 | −330 | 1568 | −310 | 1560 | −378 | 1520 | −360 | 1510 |
| Avg | 292 | 1478 | 265 | 1512 | 381 | 1394 | 373 | 1392 |

The first column in the above table indicates the location (1-8) at which the field strength measurement is made. As shown in FIG. 26A, locations 1-4 are on the perimeter of each of the four magnets at the edge diagonally opposite the center of the device. Locations 5-8 are on the perimeter of the magnets but at the edge nearest the center of the device. Thus, the table includes a row that gives the average magnitude of the measurements in each of the outer locations (1-4) and each of the inner locations (5-8). The left half of the table shows the data for the two devices (A and B) when the devices are isolated from each other, while the right half of the table shows the date for the devices when they are brought together in the position shown in FIG. 26B. For each device, the column headed "Mag." gives the measured magnitude and polarity of the magnetic induction (in Gauss) at the indicated position. The column headed "Grad." shows the difference between the magnitude of the magnetic induction at the indicated position and at the center of the corresponding magnet. For the right half of the table, it is assumed for purposes of illustration that the magnitude of the induction at the center of each magnet is the same when the devices are together as when they are isolated. In fact, the magnitude should be lower when the devices are brought together.

The data indicate that the gradient of the magnetic induction between the perimeter and center of the magnet is greater when the devices are isolated than when they are together. For example, when the devices are isolated, the average field magnitude at the outer periphery (locations 1-4) of device A is 168 G and the average gradient between the center and outer periphery is 1609 G. In contrast, when the the devices are together, the average magnitude and gradient for device A's outer periphery are 320 and 1356, respectively. The gradient is thus significantly reduced when the devices are brought together.

Figure 27:
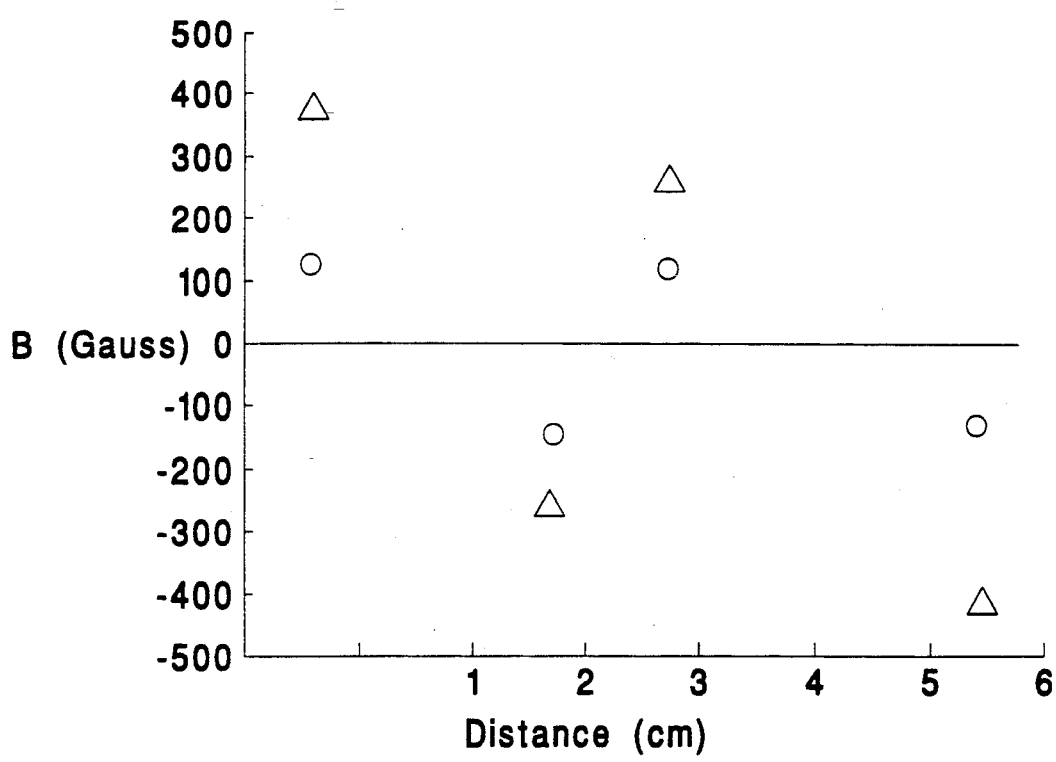
FIG. 27 is a graph showing the magnetic field data for the devices of FIGS. 26A–B.

Another way of considering the effect on the magnetic induction gradient of bringing the two devices together is shown in FIG. 27. Line X—X' in FIGS. 26A and 26B pass through points 1 and 2 on each of the devices A and B. The measured magnetic inductions at those points are plotted in FIG. 27. The data are plotted first (with triangles) for the condition in which the two devices are together. The horizontal axis is distance along line X—X' from the edge of device A. The data re then plotted (with circles) for each of the devices when isolated, but shown on the graph as though the devices were located next to each other. The data again illustrate that the magnitude of the magnetic induction at the edges of the magnets (along line X—X') is higher when the devices are together than when they are apart. A greater field strength at the edge of the magnet indicates that there is a shallower gradient in the field from the edge to the center of the pole.

All the data indicate that the octapolar (four-magnet) configuration is the effective embodiment in bringing about an effective sustained physiological effect (see FIGS. 28 A-F). This arrangement generates a different flux field with a different horizontal and vertical gradient than does the eight-magnet array, or the two-, sixteen-, or other four-magnet arrays tested. This is further illustrated by the following mathematical analysis.

MATHEMATICAL ANALYSIS

The effects of the method of the invention, at least in part, are brought about by the octapolar, alternating, symmetric, static magnetic field impingement upon the cell walls of neurons. It is believed that the steep gradient of this field brings about a polarization of the lipoprotein matrix of the cell wall such that sodium and calcium channels are blocked in such a fashion as to impede the flux of these ions. Impedance of ion flux blocks the pacemaker effect of damaged or insulted neuronal cell wall membranes (i.e., blocks initiation of a spontaneous depolarization).

The data presented above show that the square array of center-charged magnetic bodies suppresses the firing of nerve action potentials as long as the four poles on one side of the array have alternating polarity. This array is equivalent to the octapole moment known as $O_{xyz}$, as described in J. P. Wikswo, Jr. and K. R. Swinney, "Scalar multipole expansions and their dipole equivalents," *Journal of Applied Physics*, vol. 57(9), pp. 4301-4308, 1985; and J. P. Wikswo, Jr. and K. R. Swinney, "A comparison of scalar multipole expansions," *Journal of Applied Physics*, vol. 56(11), pp. 3039-3049, 1984, both of which are incorporated herein by reference. Alternative magnet arrays using a larger or smaller number of magnets, or with different arrangements of polarity are either less effective or totally ineffective. While the mechanism of action of the magnetic field on the nerve is unknown, experimental evidence suggests that the particular combination of magnetic field and field gradient provided by center-charged magnets in the $O_{xyz}$ configuration is crucial. The mathematics describing the magnetic field and field gradients produced by arrays of magnets is discussed below.

The vector magnetic induction field $\vec{B}$ at a point $\vec{r}$ produced by a center-charged magnet at point $\vec{r}'$ can be approximated, to first order, by the magnetic induction field of a magnetic dipole moment $\vec{m}$ $$\vec{B}(\vec{r}) = \frac{\mu_o}{4\pi} \left( \frac{3\vec{m} \cdot (\vec{r} - \vec{r}')}{|\vec{r} - \vec{r}'|^5} (\vec{r} - \vec{r}') - \frac{\vec{m}}{|\vec{r} - \vec{r}'|^3} \right), \quad (1)$$

where $\mu_o$ is the magnetic permeability of free space, equal to $4\pi \times 10^7$ Tesla-meter/amp ($TmA^{-1}$). If x, y, and z are the Cartesian components of $\vec{r}$, and if $m_x$, $m_y$, and $m_z$ are the components of $\vec{m}$, then $\vec{m} \cdot \vec{r}$, which represents the dot product between the two vectors, is defined by $$\vec{m} \cdot \vec{r} = m_x x + m_y y + m_z z. \quad (2)$$

In Eq. (1), $|\vec{r} - \vec{r}'|$ represents the magnitude of the vector between the points $\vec{r}$ and $\vec{r}'$, given as $$|\vec{r} - \vec{r}'| = [(x-x')^2 + (y-y')^2 + (z-z')^2]^{\frac{1}{2}}, \quad (3)$$

This can also be written as $$\vec{B}(\vec{r}) = \frac{\mu_o}{4\pi} \frac{1}{|\vec{r} - \vec{r}'|^5} \{3\vec{m} \cdot (\vec{r} - \vec{r}')(\vec{r} - \vec{r}') - \quad (4)$$

$$\vec{m}(\vec{r} - \vec{r}') \cdot (\vec{r} - \vec{r}')\}$$

Figure 32:
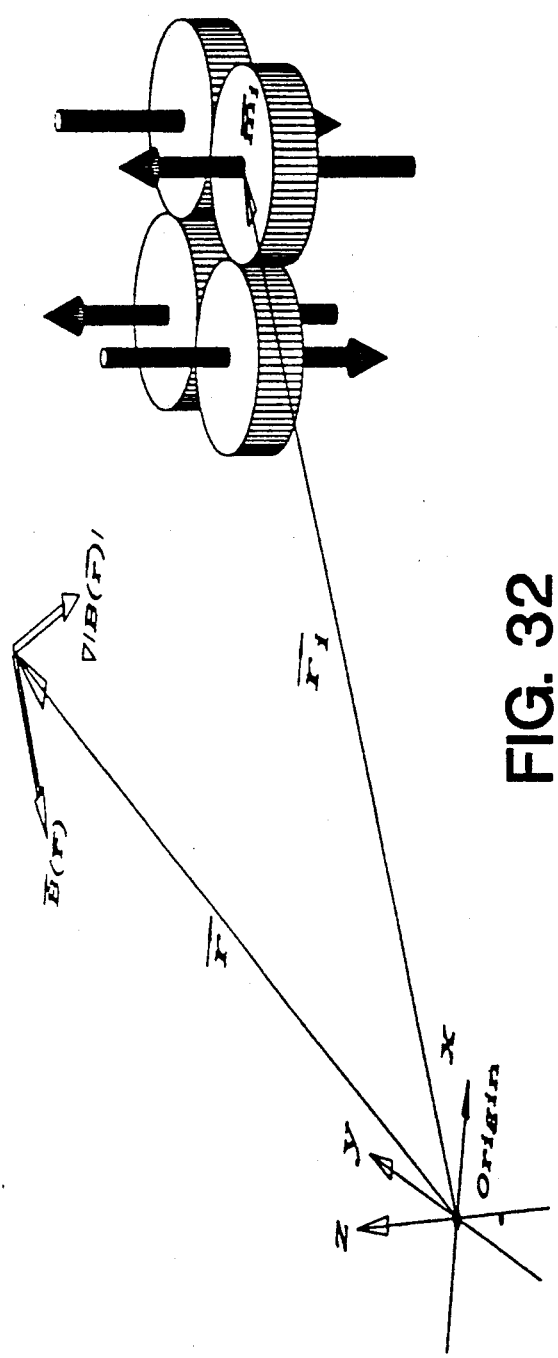
FIG. 32 illustrates the magnet geometry assumed in calculations of the magnetic field and field gradient about the magnetic device of FIG. 2.

If there are n magnets in the array, then the net magnetic field is the vector sum of the contributions of the individual magnets, i.e.

$$\vec{B}(\vec{r}) = \frac{\mu_o}{4\pi} \sum_{i=1}^{n} \left( \frac{3\vec{m_i} \cdot (\vec{r} - \vec{r_i}')}{|\vec{r} - \vec{r_i}'|^5} (\vec{r} - \vec{r_i}') - \frac{\vec{m_i}}{|\vec{r} - \vec{r_i}'|^3} \right),$$

where i is an index, ranging from 1 to n, identifying the individual magnets in the array, and $\vec{r_i}'$ is the vector describing the location of the center of the i$^{th}$ magnet. This geometry is shown in FIG. 32.

The gradient of the magnitude of the magnetic field is given by $$\nabla|\vec{B(r)}| = \frac{\partial|\vec{B(r)}|}{\partial x}\hat{i} + \frac{\partial|\vec{B(r)}|}{\partial y}\hat{j} + \frac{\partial|\vec{B(r)}|}{\partial z}\hat{k}, \quad (6)$$

where $\hat{i}, \hat{j}, \hat{k}$ are unit vectors in the x, y, and z directions, respectively and $|\vec{B}|$ is the magnitude of $\vec{B}$, computed by the Pythagorean sum of the components Since the expressions generated by applying Eq. (6) to Eq. (5) are rather complex, the analysis can be simplified by being restricted to magnet arrays lying $$|\vec{B}| = \{\vec{B}\cdot\vec{B}\}^{\frac{1}{2}} = \{B_x^2 + B_y^2 + B_z^2\}^{\frac{1}{2}}. \quad (7)$$

in the x-y plane, so that the dipoles only have a single component $m_z$. If the north pole is facing up, $m_z$ will be positive. If it is pointing down, $m_z$ will be negative. In this case, Eq. (5) reduces to $$\vec{B(r)} = \frac{\mu_o}{4\pi}\sum_{i=1}^{n}\left(\frac{3m_i\cdot(z-z')}{|r-r'|^5}(\vec{r}-\vec{r_i}) - \frac{\vec{m_i}}{|r-r'|^3}\hat{k}\right). \quad (8)$$

There are several possible mechanisms by which the magnetic induction field produced by the magnetic device might interact with a neuron. If the active neuronal mechanism is the result of either a translational force on an extended linear current element flowing in a magnetic field, or a rotational torque on either an intrinsic magnetic dipole moment or a small current loop, then the strength of the interaction will depend primarily on the magnitude of the applied field $|\vec{B}|$. It follows by dotting Eq. (4) into itself that for a single dipole $$|\vec{B}| = \frac{\mu_o}{4\pi}\frac{1}{|r-r'|^4}\{3[\vec{m}\cdot(\vec{r}-\vec{r'})]^2 + \quad (9)$$

$$[(\vec{r}-\vec{r'})\cdot(\vec{r}-\vec{r'})]\vec{m}\cdot\vec{m}\}^{\frac{1}{2}}$$

For the array of dipoles, $|\vec{B}|$ could be computed analytically by computing all of the dot products resulting from dotting Eq. (5) into itself. It would in practice by vastly easier to compute the three components of the summed field, $\vec{B}_{tot}$, and then to compute $\vec{B}_{tot}\cdot\vec{B}_{tot}$ numerically.

The magnitude of the magnetic field of the entire array is *not* equal to the sum of the magnitudes of the fields of the individual components, i.e.

$$|\vec{B}_{tot}| \neq \sum_{i=1}^{n}|\vec{B}_i|. \quad (10)$$

The only case in which the magnitude of the total field equals the sum of the magnitudes of the two individual fields is when the two individual fields are exactly the same. In any case, the total field magnitude will be less than the summed magnitudes of the individual fields. The magnitude of the total field is determined by the non-linear operation in Eq. (7), and thus field magnitudes do not obey the principle of superposition. Thus the spatial distribution of the magnitude of the magnetic field produced an isolated 4-element array will *not* be equivalent to that produced by four elements of a larger, 16-element array.

Another possibility is that the observed neurological effects could be due to a translational force applied to a biological magnetic dipole moment $\vec{m}^b$. For example, a component of one of the biological molecules involved in the generation of the spike activity may have a paramagnetic dipole moment. There are at least two different interactions between such a dipole and the externally-applied field. Application of a strong, uniform magnetic field could cause a torque on this dipole. However, the experimental data suggest that this is not the dominant mechanism.

Alternatively, a magnetic field gradient could result in a translational force being applied to the molecular component. The force, $\vec{F}$, on such a dipole is given by $$\vec{F} = (\vec{m}^b\cdot\nabla)\vec{B}. \quad (11)$$

Since $\vec{m}\cdot\nabla$ is a scalar operator acting on all three components of $\vec{B}$, it is more instructive to write this in expanded notation $$\vec{F} = \left(m_x^b\frac{\partial}{\partial x} + m_y^b\frac{\partial}{\partial y} + m_z^b\frac{\partial}{\partial z}\right)\vec{B}. \quad (12)$$

$$F_x = m_x^b\frac{\partial B_x}{\partial x} + m_y^b\frac{\partial B_x}{\partial y} + m_z^b\frac{\partial B_x}{\partial z}. \quad (13)$$

As before, the magnitude of $\vec{F}$ is obtained by the dot product

One possible mechanism by which random molecular dipoles might be oriented is through the rotational torque produced by the field itself. For $$|\vec{F}|^2 = \vec{F}\cdot\vec{F} \quad (14)$$

$$|\vec{F}|^2 = [(\vec{m}^b\cdot\nabla)\vec{B}]\cdot[(\vec{m}^b\cdot\nabla)\vec{B}] \quad (15)$$

$$|\vec{F}|^2 = (m^b\cdot\nabla)^2|\vec{B}|^2 \quad (16)$$

example, the molecular dipoles may act as a Langevin paramagnet. If the field is sufficiently strong to overcome the thermal forces acting on the molecule, then the dipole moment $\vec{m}$ will be parallel to the applied field, i.e.

$$\vec{m}^b = \beta\frac{\vec{B}}{|\vec{B}|}, \quad (17)$$

here $\beta$ represents the strength of the molecular moment and the quantity $\vec{B}$ divided by $|\vec{B}|$ simply represents a unit vector parallel to the field. In this case, $$\vec{F} = \frac{\beta}{|\vec{B}|}(\vec{B}\cdot\nabla)\vec{B} = \frac{1}{2}\frac{\beta}{|B|}\nabla|\vec{B}|^2, \quad (18)$$

using the vector identity $(\vec{B}\cdot\nabla)\vec{B} = \frac{1}{2}\{\nabla(\vec{B}\cdot\vec{B}) - \vec{B}\times(\nabla\times\vec{B})\}$ and the fact that for the fields outside a magnet $\nabla\times\vec{B} = 0$.

Alternatively, the key protein component may be diamagnetic, so that the magnetic dipole moment is induced by the field itself. In this case, $$\vec{m}^b = \gamma\vec{B}, \quad (19)$$

where $\gamma$ is related to the diamagnetic susceptibility, so that $$F = \gamma(\vec{B}\cdot\nabla)\vec{B} \quad (20)$$

$$F = \frac{1}{2}\gamma\nabla|\vec{B}|^2 \quad (21).$$

There is also the possibility that the effect involves local changes in the magnetic pressure on magnetically-susceptible objects that results from field gradients. If different components have differing magnetic susceptibilities, then there will be differential buoyant forces acting on the components. For example, membrane surface proteins might be forced deeper into the protein, thereby blocking their action, or membrane-spanning proteins may be lifted so that they no longer span the membrane. As a first-order approximation, such forces might be modeled as $$F \alpha |\vec{B}| \nabla |\vec{B}|. \quad (22)$$

Thus, there are several possible mechanisms by which the $O_{xyz}$ magnet configuration might interact with neurons. It could be through the total magnetic field, given by Eq. (5); by the gradient in the total magnetic field given by Eq. (6); by components of the gradient squared acting on the magnitude-squared, as given by Eq. (16); by the reciprocal of magnitude times the gradient of the magnitude-squared, as given by Eq. (18); simply by the gradient of the magnitude-squared, as given by Eq. (21); or by the magnitude times the gradient of the magnitude, as given by Eq. (22).

The effects appear to be determined by the gradient of the field magnitude, possibly in conjunction with the field magnitude, and not by the field magnitude alone. The principle of linear superposition of fields does not apply to the quantities of greatest neurological significance. Thus the effects of four magnetic bodies in isolation are different from the effects of four magnetic bodies that are part of a much larger array. The experimental evidence indicates that the neurological efficacy of the center-charged permanent magnets in the $O_{xyz}$ configuration arises from the particular combination of fields and field gradients. Other configurations will provide different combinations of fields and field gradients, and hence it is not surprising that these other configurations demonstrate substantially reduced or nonexistent neurological effects.

What is claimed is:

1. A method of suppressing action potentials of a neuron, comprising the steps of:
   assembling an octapolar group of magnetic bodies having two positive circular magnetic poles and two negative circular magnetic poles of approximately equal strength substantially in a first plane;
   orienting said two positive poles and said two negative poles of said group of magnetic bodies in said first plane to define the four vertices of a rectangular shape with said two positive poles defining two diagonal vertices and said two negative poles defining opposite vertices of said rectangular shape;
   fixing said orientation of said group of magnetic bodies in a housing such that the magnetic bodies are sufficiently close that the magnetic induction produced by each of said poles has a significant magnitude at the location of each of the other of said poles; and
   selectively placing said housing at a distance from the neuron such that said group of magnetic bodies generates a biologically effective magnetic field at the neuron.

2. The method of claim 1, wherein said step of assembling an octapolar group of magnetic bodies comprises assembling four substantially identical cylinders of magnetic material, each of said cylinders having two opposite end faces, one of said two end faces having a positive magnetic pole thereon and the other of said two end faces having a negative magnetic pole thereon, the positive magnetic pole end faces of two of said cylinders and the negative magnetic pole end faces of two of said cylinders being in said first plane, and the opposite magnetic pole end faces of two of said cylinders and the positive pole end faces of two of said cylinders being in a second plane, with all cylinders being center charged.

3. The method of claim 2, wherein said step of assembling four substantially identical cylinders comprises assembling four cylindrical neodymium magnets having a diameter of between approximately 0.25" (0.63 cm) to 0.50" (1.27 cm) and having an energy product of approximately 25 MG-Oe.

4. The method of claim 1 wherein the step of orienting said positive poles and said negative poles comprises orienting said poles so that the distance from the center of one of said poles to an adjacent one of said poles is less than three times the diameter of said poles.

5. The method of claim 1, wherein the step of placing said housing comprises placing said housing so that said distance from the neuron to said first plane is less than five times the diameter of said poles.

6. A device for generating a magnetic flux against a neuron, consisting essentially of:
   an octapolar group of four magnetic bodies having two positive circular magnetic poles and two negative circular magnetic poles of approximately equal strength and lying substantially in a first plane, said magnetic bodies being disposed in an orientation such that said two positive poles and said two negative poles lying in said first plane define the four vertices of a rectangular shape with said two positive poles defining two diagonal vertices and said two negative poles defining opposite vertices of said rectangular shape, such that said magnetic bodies are sufficiently close that the magnetic induction produced by each of said poles has a significant magnitude at the location of each of the other of said poles, and such that said magnetic bodies are sufficiently distant from other sources of magnetic induction that the magnetic induction field generated by said magnetic bodies is not substantially distorted; and
   a housing maintaining said magnetic bodies in said orientation.

7. The device of claim 6, further comprising means for fixing said housing at a distance from the neuron such that said group of magnetic bodies generates a biologically effective magnetic field at the neuron.

8. The device of claim 6, wherein each of said four magnetic bodies are substantially identical cylinders, each of said cylinders having two opposite end faces, one of said two end faces having a positive magnetic pole thereon and the other of said two end faces having a negative magnetic pole thereon, the positive magnetic pole end faces of two of said cylinders and the negative magnetic pole end faces of two of said cylinders being in said first plane, and the opposite magnetic pole end faces of two of said cylinders and the positive pole end faces of two of said cylinders being in a second plane, with all cylinders being center charged.

9. The permanent magnet device of claim 8, wherein each of said magnetic cylinders comprises a neodymium magnet.

10. The permanent magnet device of claim 9, wherein each of said neodymium magnet cylinders has a diameter in the range of 0.25 "(0.63 cm) to 0.50" (1.27 cm).

11. The permanent magnet device of claim 10, wherein each of said neodymium magnets has an energy product of approximately 25 MG-Oe.

12. The permanent magnet device of claim 16, wherein said rectangular shape is a square.

13. The permanent magnet device of claim 6, wherein the distance from the center of one of said poles to an adjacent one of said poles is less than three times the diameter of said poles.

14. The permanent magnet device of claim 7, wherein said distance from the neuron to said first plane is less than five times the diameter of said poles.

* * * * *